(12) United States Patent
Collis et al.

(10) Patent No.: US 7,479,501 B2
(45) Date of Patent: Jan. 20, 2009

(54) HETEROARYL-CYCLIC ACETALS

(75) Inventors: Alan Collis, Basking Ridge, NJ (US); Frank Halley, Sèvres (FR); Iain McLay, Loughton (GB)

(73) Assignee: Aventis Pharma Limited, Kent (GB)

( * ) Notice: Subject to any disclaimer, the term of this patent is extended or adjusted under 35 U.S.C. 154(b) by 841 days.

(21) Appl. No.: 09/871,564

(22) Filed: May 31, 2001

(65) Prior Publication Data

US 2005/0090501 A1   Apr. 28, 2005

Related U.S. Application Data

(63) Continuation of application No. PCT/GB99/04283, filed on Dec. 16, 1999.

(60) Provisional application No. 60/122,425, filed on Mar. 2, 1999.

(30) Foreign Application Priority Data

Dec. 16, 1998  (GB) .................................. 9827721.3

(51) Int. Cl.
  *A61K 31/4439*  (2006.01)
  *C07D 405/14*  (2006.01)
(52) U.S. Cl. .................................... 514/341; 546/275.4
(58) Field of Classification Search .............. 546/275.4; 514/341
  See application file for complete search history.

(56) References Cited

U.S. PATENT DOCUMENTS 4,659,503 A   4/1987   Eidenschink

FOREIGN PATENT DOCUMENTS

| EP | 0146862 | 7/1985 |
|---|---|---|
| EP | 0506437 | 9/1992 |
| WO | WO98/52937 | 11/1998 |
| WO | WO98/52940 | 11/1998 |
| WO | WO98/52941 | 11/1998 |
| WO | WO98/56377 | 12/1998 |
| WO | WO98/56788 | 12/1998 |

Primary Examiner—Patricia L Morris
(74) Attorney, Agent, or Firm—Raymond S. Parker

(57) ABSTRACT

Compounds of formula (I) are described in which Het is a five or six membered heteroaromatic ring of the formula

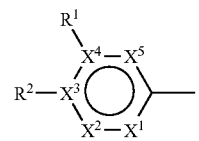

in which one of $R^1$ and $R^2$ is optionally substituted heteroaryl and the other is optionally substituted heteroaryl or optionally substituted aryl; $X^1$ is a bond, $X^3$ and $X^4$ are each independently N or C and $X^2$ and $X^5$ are independently CH, N, NH, O or S; or $X^3$ and $X^4$ are C, one of $X^1$, $X^2$ and $X^5$ is N and the others are N or CH; but excluding compounds in which $X^1$ is a bond, one of $X^2$ and $X^5$ is N and the other is NH and $X^3$ and $X^4$ are both C; $R^3$ represents a group $-L^1-R^6$; $R^4$ represents hydrogen, alkyl or hydroxyalkyl; or $R^3$ and $R^4$, when attached to the same carbon atom, may form with the said carbon atom a cycloalkyl, cycloalkenyl or heterocycloalkyl ring or a group $C=CH_2$; $R^5$ represents hydrogen or alkyl; and m is zero or an integer 1 or 2; and N-oxides thereof, and their prodrugs; and pharmaceutically acceptable salts and solvates of compounds of formula (I) and N-oxides thereof, and their prodrugs.

The compounds are TNF inhibitors and are useful as pharmaceuticals.

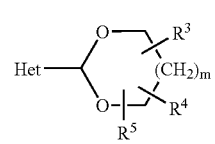

(I)

5 Claims, No Drawings

HETEROARYL-CYCLIC ACETALS

CROSS-REFERENCE TO RELATED APPLICATION

This application is a continuation of PCT/GB99/04283 filed Dec. 16, 1999, which, in turn, claims priority of GB Application No. 9827721.3, filed Dec. 16, 1998 and U.S. Provisional Application No. 60/122,425 filed Mar. 2, 1999.

FIELD OF THE INVENTION

This invention is directed to heteroaryl-cyclic acetals, their preparation, pharmaceutical compositions containing these compounds, and their pharmaceutical use in the treatment of disease states capable of being modulated by the inhibition of TNF.

BACKGROUND OF THE INVENTION

Tumour necrosis factor (TNF) is an important pro-inflammatory cytokine which causes hemorrhagic necrosis of tumors and possesses other important biological activities. TNF is released by activated macrophages, activated T-lymphocytes, natural killer cells, mast cells and basophils, fibroblasts, endothelial cells and brain astrocytes among other cells.

The principal in vivo actions of TNF can be broadly classified as inflammatory and catabolic. It has been implicated as a mediator of endotoxic shock, inflammation of joints and of the airways, immune deficiency states, allograft rejection, and in the cachexia associated with malignant disease and some parasitic infections. In view of the association of high serum levels of TNF with poor prognosis in sepsis, graft versus host disease and adult respiratory distress syndrome, and its role in many other immunologic processes, this factor is regarded as an important mediator of general inflammation.

TNF primes or activates neutrophils, eosinophils, and endothelial cells to release tissue damaging mediators and increase the expression of adhesion molecules. In fibroblasts, TNF stimulates the production of collagenase, an enzyme implicated in the joint destruction in rheumatoid arthritis. TNF also activates monocytes, macrophages and T-lymphocytes to cause the production of colony stimulating factors and other pro-inflammatory cytokines such IL-1, IL-6, IL-8 and GM-CSF, which in some cases mediate the end effects of TNF. The ability of TNF to activate T-lymphocytes, monocytes, macrophages and related cells has been implicated in the progression of Human Immunodeficiency Virus (HIV) infection. In order for these cells to become infected with HIV and for HIV replication to take place the cells must be maintained in an activated state. Cytokines such as TNF have been shown to activate HIV replication in monocytes and macrophages. Features of endotoxic shock such as fever, metabolic acidosis, hypotension and intravascular coagulation are thought to be mediated through the actions of TNF. The cachexia associated with certain disease states is mediated through indirect effects on protein catabolism. TNF also promotes bone resorption and acute phase protein synthesis.

TNF-alpha inhibits surfactant protein C gene transcription, which may contribute to abnormalities of surfactant homeostasis associated with pulmonary injury and infection, induces mucin hypersecretion and mediates the recruitment of neutrophils and eosinophils during airway inflammation. Although TNF-alpha inhibits collagen synthesis in fibroblasts, a number of studies point to it being pro-fibrotic in vivo. Thus, by inhibiting TNF-alpha production, the compounds of the invention have potential in suppressing the inflammation and airways remodelling that occurs in asthma.

TNF-alpha inhibits the ability of insulin to stimulate glucose uptake in adipose tissue. In obesity the overproduction of TNF is thought to cause an insulin-resistant state. Thus, by blocking TNF release the compounds of the invention have anti-diabetic potential.

TNF-alpha can induce angiogenesis in normally avascular tissue, possibly through upregulation of other pro-inflammatory cytokines, upregulation of adhesion molecules, stimulation of matrix mettalloproteinase expression and increased prostaglandin production. Thus, inhibition of TNF-alpha release by compounds of the invention will have benefit in angiogenesis dependent diseases including arthritis, diabetic retinopathies and ischemia induced diseases (myocardial infarction) and cancer.

The discussion herein relates to disease states associated with TNF including those disease states related to the production of TNF itself, and disease states associated with other cytokines, such as, but not limited to IL-1 or IL-6, that are modulated by association with TNF. For example, a IL-1 associated disease state, where IL-1 production or action is exacerbated or secreted in response to TNF, would therefore be considered a disease state associated with TNF. TNF-alpha and TNF-beta are also herein referred to collectively as "TNF" unless specifically delineated otherwise, since there is a close structural homology between TNF-alpha (cachectin) and TNF-beta (lymphotoxin) and each of them has a capacity to induce similar biological responses and bind to the same cellular receptor.

SUMMARY OF THE INVENTION

We have now found a novel group of heteroaryl-cyclic acetals which have valuable pharmaceutical properties, in particular the ability to regulate proteins that mediate cellular activity, for example TNF.

Thus, in one aspect, the present invention is directed to compounds of general formula (I)

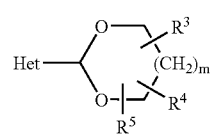

wherein:—

Het is a five or six membered heteroaromatic ring of the formula

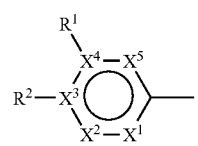

in which one of $R^1$ and $R^2$ is optionally substituted heteroaryl and the other is optionally substituted heteroaryl or optionally substituted aryl; $X^1$ is a bond, $X^3$ and $X^4$ are each independently N or C and $X^2$ and $X^5$ are independently CH, N, NH, O or S; or $X^3$ and $X^4$ are C, one of $X^1$, $X^2$ and $X^5$ is N and the others are N or CH; but excluding compounds in which $X^1$ is a bond, one of $X^2$ and $X^5$ is N and the other is NH and $X^3$ and $X^4$ are both C;

$R^3$ represents a group -$L^1$-$R^6$;

$R^4$ represents hydrogen, alkyl or hydroxyalkyl; or $R^3$ and $R^4$, when attached to the same carbon atom, may form with the said carbon atom a cycloalkyl, cycloalkenyl or heterocycloalkyl ring or a group C=$CH_2$;

$R^5$ represents hydrogen or alkyl;

$R^6$ is hydrogen, alkyl, azido, hydroxy, alkoxy, aryl, arylalkyloxy, aryloxy, carboxy (or an acid bioisostere), cycloalkyl, cycloalkyloxy, heteroaryl, heteroarylalkyloxy, heteroaryloxy, heterocycloalkyl, heterocycloalkyloxy, nitro, —$NY^1Y^2$, —$N(R^7)$—C(=Z)—$R^8$, —$N(R^7)$—C(=Z)-$L^2$-$R^9$, —NH—C(=Z)—NH—$R^8$, —NH—C(=Z)—NH-$L^2$-$R^9$, —$N(R^7)$—$SO_2$—$R^8$, —$N(R^7)$—$SO_2$-$L^2$-$R^9$, —S(O)$_n R^{10}$, —C(=Z)—$NY^1Y^2$ or —C(=Z)—$OR^{10}$;

$R^7$ is hydrogen, alkyl, aryl, arylalkyl, cycloalkyl, heteroaryl, heteroarylalkyl, or heterocycloalkyl;

$R^8$ is alkyl, alkoxy, aryl, arylalkyloxy, cycloalkyl, heteroaryl, heteroarylalkyloxy or heterocycloalkyl;

$R^9$ is alkoxy, aryl, arylalkyloxy, arylalkyloxycarbonylamino, carboxy (or an acid bioisostere), cycloalkyl, cyano, halo, heteroaryl, heteroarylalkoxy, heterocycloalkyl, hydroxy or —$NY^3Y^4$;

$R^{10}$ is alkyl, aryl, arylalkyl, cycloalkyl, heteroaryl, heteroarylalkyl, or heterocycloalkyl;

$L^1$ represents a direct bond or a straight- or branched-chain alkylene linkage containing from 1 to about 6 carbon atoms and optionally substituted by halogen, hydroxy, alkoxy or oxo;

$L^2$ is a straight- or branched-chain alkylene linkage containing from 1 to about 6 carbon atoms;

$Y^1$ and $Y^2$ are independently hydrogen, alkenyl, alkynyl, aryl, cycloalkyl, heterocycloalkyl, heteroaryl or alkyl optionally substituted by alkoxy, aryl, cyano, cycloalkyl, heteroaryl, heterocycloalkyl, hydroxy, oxo, —$CO_2R^7$, —$CONY^3Y^4$ or —$NY^3Y^4$, or the group —$NY^1Y^2$ may form a 5-7 membered cyclic amine which (i) may be optionally substituted with one or more substituents selected from alkoxy, carboxamido, carboxy, hydroxy, oxo (or a 5, 6,or 7 membered cyclic acetal derivative thereof), alkyl, aryl, arylalkyl, cycloalkyl, heteroaryl, heteroarylalkyl, or heterocycloalkyl or alkyl substituted by carboxy, carboxamido or hydroxy (ii) may also contain a further heteroatom selected from O, S, $SO_2$ or $NY^5$ and (iii) may also be fused to additional aryl, heteroaryl, heterocycloalkyl or cycloalkyl rings to form a bicyclic or tricyclic ring system;

$Y^3$ and $Y^4$ are independently hydrogen, alkenyl, alkyl, alkynyl, aryl, arylalkyl, cycloalkyl, heteroaryl or heteroarylalkyl, or the group —$NY^3Y^4$ may form a 5-7 membered cyclic amine as defined for —$NY^1Y^2$ above;

$Y^5$ is hydrogen, alkyl, aryl, arylalkyl, —C(=Z)$R^{10}$, —C(=Z)$OR^{10}$ or —$SO_2R^{10}$;

Z is an oxygen or sulphur atom;

m is zero or an integer 1 or 2; and n is zero or an integer 1 or 2;

and N-oxides thereof, and their prodrugs; and pharmaceutically acceptable salts and solvates (e.g. hydrates) of compounds of formula (I) and N-oxides thereof, and their prodrugs.

DETAILED DESCRIPTION OF THE INVENTION

In the present specification, the term "compounds of the invention", and equivalent expressions, are meant to embrace compounds of general formula (I) as hereinbefore described, which expression includes the N-oxides, the prodrugs, the pharmaceutically acceptable salts, and the solvates, e.g. hydrates, where the context so permits. Similarly, reference to intermediates, whether or not they themselves are claimed, is meant to embrace their N-oxides, salts, and solvates, where the context so permits. For the sake of clarity, particular instances when the context so permits are sometimes indicated in the text, but these instances are purely illustrative and it is not intended to exclude other instances when the context so permits.

It will be appreciated that when m is zero the cyclic acetal system in formula (I) represents a 1,3-dioxolane ring; when m is 1 the cyclic acetal system in formula (I) represents a 1,3-dioxane; and when m is 2 the cyclic acetal system in formula (I) represents a 1,3-dioxepane.

As used above, and throughout the description of the invention, the following terms, unless otherwise indicated, shall be understood to have the following meanings:

"Patient" includes both human and other mammals.

"Acid bioisostere" means a group which has chemical and physical similarities producing broadly similar biological properties to a carboxy group (see Lipinski, Annual Reports in Medicinal Chemistry, 1986, 21, page 283 "Bioisosterism In Drug Design"; Yun, Hwahak Sekye, 1993, 33, pages 576-579 "Application Of Bioisosterism To New Drug Design"; Zhao, Huaxue Tongbao, 1995, pages 34-38 "Bioisosteric Replacement And Development Of Lead Compounds In Drug Design"; Graham, Theochem, 1995, 343, pages 105-109 "Theoretical Studies Applied To Drug Design:ab initio Electronic Distributions In Bioisosteres"). Examples of suitable acid bioisosteres include: —C(=O)—NHOH, —C(=O)—$CH_2OH$, —C(=O)—$CH_2SH$, —C(=O)—NH—CN, sulpho, phosphono, alkylsulphonylcarbamoyl, tetrazolyl, arylsulphonylcarbamoyl, heteroarylsulphonylcarbamoyl, N-methoxycarbamoyl, 3-hydroxy-3-cyclobutene-1, 2-dione, 3,5-dioxo-1,2,4-oxadiazolidinyl or heterocyclic phenols such as 3-hydroxyisoxazolyl and 3-hydoxy-1-methylpyrazolyl.

"Acyl" means an H—CO— or alkyl-CO— group in which the alkyl group is as described herein.

"Acylamino" is an acyl-NH— group wherein acyl is as defined herein.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably about 2 to about 4 carbon atoms in the chain. "Branched", as used herein and throughout the text, means that one or more lower alkyl groups such as methyl, ethyl or propyl are attached to a linear chain; here a linear alkenyl chain. "Lower alkenyl" means about 2 to about 4 carbon atoms in the chain which may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Alkoxy" means an alkyl-O— group in which the alkyl group is as described herein. Exemplary alkoxy groups include methoxy, ethoxy, n-propoxy, i-propoxy, n-butoxy and heptoxy.

"Alkoxymethyl" means an alkyl-O—$CH_2$— group in which the alkyl group is as described herein. Exemplary alkoxymethyl groups include methoxymethyl and ethoxymethyl.

"Alkoxycarbonyl" means an alkyl-O—CO— group in which the alkyl group is as described herein. Exemplary alkoxycarbonyl groups include methoxy- and ethoxycarbonyl.

"Alkyl" means, unless otherwise specified, as a group or part of a group, an aliphatic hydrocarbon group which may be straight or branched having about 1 to about 15 carbon atoms in the chain optionally substituted by one or more halogen atoms. Particular alkyl groups have from 1 to about 6 carbon atoms. "Lower alkyl" as a group or part of a lower alkoxy, lower alkylthio, lower alkylsulphinyl or lower alkylsulphonyl group means unless otherwise specified, an aliphatic hydrocarbon group which may be straight or branched having about 1 to about 4 carbon atoms in the chain. Exemplary alkyl groups include methyl, ethyl, n-propyl, i-propyl, n-butyl, s-butyl, t-butyl, n-pentyl, 3-pentyl, heptyl, octyl, nonyl, decyl and dodecyl.

"Alkylene" means a straight or branched bivalent hydrocarbon chain having from 1 to about 8 carbon atoms. Particular alkylene groups are the lower alkylene groups having from 1 to about 6 carbon atoms. Exemplary groups include methylene and ethylene.

"Alkylenedioxy" means an —O-alkyl-O— group in which the alkyl group is as defined above. Exemplary alkylenedioxy groups include methylenedioxy and ethylenedioxy.

"Alkylsulphinyl" means an alkyl-SO— group in which the alkyl group is as previously described. Preferred groups are those in which the alkyl group is $C_{1-4}$alkyl.

"Alkylsulphonyl" means an alkyl-$SO_2$— group in which the alkyl group is as previously described. Preferred groups are those in which the alkyl group is $C_{1-4}$alkyl.

"Alkylsulphonylcarbamoyl" means an alkyl-$SO_2$—NH—C(=O)— group in which the alkyl group is as previously described. Preferred alkylsulphonylcarbamoyl groups are those in which the alkyl group is $C_{1-4}$alkyl.

"Alkylthio" means an alkyl-S— group in which the alkyl group is as previously described. Exemplary alkylthio groups include methylthio, ethylthio, isopropylthio and heptylthio.

"Alkynyl" means an aliphatic hydrocarbon group containing a carbon-carbon triple bond and which may be straight or branched having about 2 to about 15 carbon atoms in the chain. Preferred alkynyl groups have 2 to about 12 carbon atoms in the chain; and more preferably about 2 to about 4 carbon atoms in the chain. Exemplary alkynyl groups include ethynyl, propynyl, n-butynyl, i-butynyl, 3-methylbut-2-ynyl, and n-pentynyl.

"Aroyl" means an aryl-CO— group in which the aryl group is as described herein. Exemplary groups include benzoyl and 1- and 2-naphthoyl.

"Aroylamino" is an aroyl-NH— group wherein aroyl is as previously defined.

"Aryl" as a group or part of a group denotes: (i) an optionally substituted monocyclic or multicyclic aromatic carbocyclic moiety of about 6 to about 14 carbon atoms, such as phenyl or naphthyl; or (ii) an optionally substituted partially saturated multicyclic aromatic carbocyclic moiety in which an aryl and a cycloalkyl or cycloalkenyl group are fused together to form a cyclic structure, such as a tetrahydronaphthyl, indenyl or indanyl ring. Aryl groups may be substituted with one or more aryl group substituents which may be the same or different, where "aryl group substituent" includes, for example, acyl, acylamino, alkoxy, alkoxycarbonyl, alkylenedioxy, alkylsulphinyl, alkylsulphonyl, alkylthio, aroyl, aroylamino, aryl, arylalkyloxy, arylalkyloxycarbonyl, arylalkylthio, aryloxy, aryloxycarbonyl, arylsulphinyl, arylsulphonyl, arylthio, carboxy, cyano, halo, heteroaroyl, heteroaryl, heteroarylalkyloxy, heteroaroylamino, heteroaryloxy, hydroxy, nitro, trifluoromethyl, $Y^3Y^4N$—, $Y^3Y^4NCO$—, $Y^3Y^4NSO_2$—, $Y^3Y^4N$—$C_{2-6}$alkylene-$Z^1$- (where $Z^1$ is O, $NR^5$ or $S(O)_n$), alkylC(=O)—$Y^3N$—, alkyl$SO_2$—$Y^3N$— or alkyl optionally substituted with aryl, heteroaryl, hydroxy, or $Y^3Y^4N$—. Preferred aryl group substituents within $R^1$ and $R^2$ include halogen, alkoxy, trifluoromethyl, alkylthio, alkylsulphinyl, $Y^3Y^4N$—, alkylC(=O)—$Y^3N$— or alkyl$SO_2$—$Y^3N$—, more preferably fluoro.

"Arylalkyl" means an aryl-alkyl- group in which the aryl and alkyl moieties are as previously described. Preferred arylalkyl groups contain a $C_{1-4}$alkyl moiety. Exemplary arylalkyl groups include benzyl, 2-phenethyl and naphthlenemethyl.

"Arylalkyloxy" means an arylalkyl-O— group in which the arylalkyl groups is as previously described. Exemplary arylalkyloxy groups include benzyloxy and 1- or 2-naphthalenemethoxy.

"Arylalkyloxycarbonyl" means an arylalkyl-O—CO— group in which the arylalkyl groups is as previously described. An exemplary arylalkyloxycarbonyl group is benzyloxycarbonyl.

"Arylalkyloxycarbonylamino" means an arylalkyl-O—CO—NH— group in which the arylalkyl groups is as previously described. An exemplary arylalkyloxycarbonyl group is benzyloxycarbonylamino.

"Arylalkylthio" means an arylalkyl-S— group in which the arylalkyl group is as previously described. An exemplary arylalkylthio group is benzylthio.

"Aryloxy" means an aryl-O— group in which the aryl group is as previously described. Exemplary aryloxy groups include optionally substituted phenoxy and naphthoxy.

"Aryloxycarbonyl" means an aryl-O—CO— group in which the aryl group is as previously described. Exemplary aryloxycarbonyl groups include phenoxycarbonyl and naphthoxycarbonyl.

"Arylsulphinyl" means an aryl-SO— group in which the aryl group is as previously described.

"Arylsulphonyl" means an aryl-$SO_2$— group in which the aryl group is as previously described.

"Arylsulphonylcarbamoyl" means an aryl-$SO_2$—NH—C(=O)— group in which the aryl group is as previously described.

"Arylthio" means an aryl-S— group in which the aryl group is as previously described. Exemplary arylthio groups include phenylthio and naphthylthio.

"Azaheteroaryl" means an aromatic carbocyclic moiety of about 5 to about 10 ring members in which one of the ring members is nitrogen and the other ring members are chosen from carbon, oxygen, sulphur, or nitrogen. Examples of optionally substituted azaheteroaryl groups include pyridyl, pyrimidinyl, quinolinyl, isoquinolinyl, quinazolinyl, imidazolyl, and benzimidazolyl, optionally substituted with one or more "heteroaryl group substituents". Preferred azaheteroaryl groups for $R^1$ and $R^2$ include optionally substituted pyridyl and pyrimidinyl. Preferred heteroaryl group substituents when $R^1$ or $R^2$ is pyrimidinyl include $R^{11}Z^2$-[where $R^{11}$ is alkyl, aryl, cycloalkyl, heteroaryl, heterocycloalkyl, or alkyl substituted by alkoxy, aryl, cyano, cycloalkyl, heteroaryl, heterocycloalkyl, hydroxy, oxo, —$CO_2R^7$, —$CONY^3Y^4$ or —$NY^1Y^2$ and $Z^2$ is O or $S(O)_n$] and $Y^1Y^2N$—.

"Cyclic amine" means a 3 to 8 membered monocyclic cycloalkyl ring system where one of the ring carbon atoms is replaced by nitrogen. Exemplary cyclic amines include pyrrolidine, piperidine, morpholine, piperazine, indoline and pyrindoline.

"Cycloalkenyl" means an optionally substituted non-aromatic monocyclic or multicyclic ring system containing at least one carbon-carbon double bond and having about 5 to about 10 carbon atoms. Particular monocyclic cycloalkenyl rings include $C_{3-7}$cycloalkenyl such as cyclopentenyl, cyclohexenyl and cyclopentenyl. Exemplary multicyclic cycloalkenyl ring include norbornenyl. The cycloalkenyl group may be substituted by one or more substituents chosen from, for example, halo, or alkyl.

"Cycloalkyl" means an optionally substituted non-aromatic monocyclic or multicyclic ring system of about 3 to about 10 carbon atoms. Particular monocyclic cycloalkyl rings include $C_{3-7}$cycloalkyl such as cyclopropyl, cyclopentyl, cyclohexyl and cycloheptyl. Exemplary multicyclic cycloalkyl rings include perhydronaphthyl, adamant-(1- or 2-)yl and norbornyl and spirocyclic groups (e.g. spiro[4,4]non-2-yl). When $R^3$ is, or contains, a cycloalkyl ring this may particularly represent a 3 to 7 membered monocyclic ring, especially cyclohexyl. The cycloalkyl group may be substituted by one or more (e.g. 1, 2, or 3) substituents chosen from, for example, alkyl, aryl, arylalkyl, halo, halo substituted alkyl (such as trifluoromethyl), hydroxyalkyl, hydroxy, alkoxy, —S(O)$_n$-alkyl, —NY$^3$Y$^4$ or —CO$_2$R$^7$.

"Cycloalkyloxy" means a cycloalkyl-O— group in which the cycloalkyl group is as described herein. Exemplary cycloalkyloxy groups include cyclopropyloxy, cyclopentyloxy, cyclohexyloxy and cycloheptyloxy.

"Halo" or "halogen" means fluoro, chloro, bromo, or iodo. Preferred are fluoro or chloro.

"Heteroaroyl" means a heteroaryl-CO— group in which the heteroaryl group is as described herein. Exemplary groups include pyridylcarbonyl.

"Heteroaroylamino" means a heteroaroyl-NH— group in which the heteroaroyl moiety is as previously described.

"Heteroaryl" as a group or part of a group denotes an optionally substituted aromatic monocyclic or multicyclic organic moiety of about 5 to about 10 ring members in which one or more of the ring members is/are element(s) other than carbon, for example nitrogen, oxygen or sulphur. Examples of suitable optionally substituted heteroaryl groups include optionally substituted benzimidazolyl, furyl, imidazolyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl groups. When $R^1$ or $R^2$ is an optionally substituted heteroaryl group this may particularly represent an optionally substituted "azaheteroaryl" group. Heteroaryl groups may be substituted with one or more heteroaryl group substituents which may be the same or different, where "heteroaryl group substituent" includes, for example acyl, acylamino, alkoxycarbonyl, alkylenedioxy, aroyl, aroylamino, aryl, arylalkyloxycarbonyl, aryloxycarbonyl, carboxy, cyano, halo, heteroaroyl, heteroaryl, heteroaroylamino, hydroxy, nitro, trifluoromethyl, $R^{11}Z^2$-, $Y^1Y^2N$—, $Y^1Y^2N$—CO—, $Y^1Y^2NSO_2$—, alkylSO$_2$—Y$^1$N— or alkyl optionally substituted with aryl, heteroaryl, hydroxy, oxo, —CO$_2$R$^7$, —CONY$^3$Y$^4$ or —NY$^1$Y$^2$.

"Heteroarylalkyl" means a heteroaryl-alkyl- group in which the heteroaryl and alkyl moieties are as previously described. Preferred heteroarylalkyl groups contain a $C_{1-4}$alkyl moiety. Exemplary heteroarylalkyl groups include pyridylmethyl.

"Heteroarylalkyloxy" means an heteroarylalkyl-O— group in which the heteroarylalkyl group is as previously described. Exemplary heteroaryloxy groups include optionally substituted pyridylmethoxy.

"Heteroaryloxy" means an heteroaryl-O— group in which the heteroaryl group is as previously described. Exemplary heteroaryloxy groups include optionally substituted pyridyloxy.

"Heteroarylsulphonylcarbamoyl" means a heteroaryl-SO$_2$—NH—C(=O)— group in which the heteroaryl group is as previously described.

"Heterocycloalkyl" means a cycloalkyl group as defined above which contains one or more heteroatoms selected from O, S or NY$^5$. Particular heterocycloalkyl groups include 5-7 membered monocyclic heterocyclic groups such as cyclic ethers containing 5-7 ring members such as tetrahydrofuran and perhydropyran.

"Heterocycloalkyloxy" means a heterocycloalkyl-O— group in which the heterocycloalkyl is as previously defined.

"Hydroxyalkyl" means a HO-alkyl- group in which alkyl is as previously defined. Preferred hydroxyalkyl groups contain $C_{1-4}$alkyl. Exemplary hydroxyalkyl groups include hydroxymethyl and 2-hydroxyethyl.

"Prodrug" means a compound which is convertible in vivo by metabolic means (e.g. by hydrolysis) to a compound of formula (I), including N-oxides thereof. For example an ester of a compound of formula (I) containing a hydroxy group may be convertible by hydrolysis in vivo to the parent molecule. Alternatively an ester of a compound of formula (I) containing a carboxy group may be convertible by hydrolysis in vivo to the parent molecule.

"Solvate" means a physical association of a compound of this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates, methanolates, and the like.

Suitable esters of compounds of formula (I) containing a hydroxy group, are for example acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methanesulphonates, ethanesulphonates, benzenesulphonates, p-toluenesulphonates, cyclohexylsulphamates and quinates.

Suitable esters of compounds of formula (I) containing a carboxy group, are for example those described by F. J. Leinweber, Drug Metab. Res., 1987, 18, page 379.

An especially useful class of esters of compounds of formula (I) containing a hydroxy group, may be formed from acid moieties selected from those described by Bundgaard et. al., J. Med. Chem., 1989, 32, page 2503-2507, and include substituted (aminomethyl)-benzoates, for example dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

Some of the compounds of the present invention are basic, and such compounds are useful in the form of the free base or in the form of a pharmaceutically acceptable acid addition salt thereof.

Acid addition salts are a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention include those derived from mineral acids and organic acids, and include hydrohalides, e.g. hydrochlorides and hydrobromides, sulphates, phosphates, nitrates, sulphamates, acetates, citrates, lactates, tartrates, malonates, oxalates, salicylates, propionates, succinates, fumarates, maleates, methylene-bis-b-hydroxynaphthoates, gentisates, isethionates, di-p-toluoyl-tartrates, methane-sulphonates, ethanesulphonates, benzene-sulphonates, p-toluenesulphonates, cyclohexylsulphamates and quinates.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations. Pharmaceutically acceptable salts, including those derived from alkali and alkaline earth metal salts, within the scope of the invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methyl-glucamine, lysine, arginine, ornithine, choline, N,N'-dibenzylethyl-enediamine, chloroprocaine, diethanolamine, procaine, N-benzylphenethylamine, diethylamine, piperazine, tris(hydroxymethyl)aminomethane, tetramethylammonium hydroxide, and the like.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

With reference to formula (I) above, the following are particular and preferred groupings:

Het may particularly represent

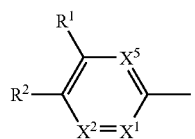

where $R^1$ and $R^2$ are as defined above, one of the atoms $X^1$, $X^2$ and $X^5$ represents N and the others independently represent N or CH. Examples of suitable ring systems include pyridyl, pyrimidinyl, pyrazinyl, pyridazinyl and triazinyl.

Het may also particularly represent

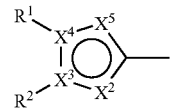

where $R^1$ and $R^2$ are as defined above, $X^2$ and $X^5$ are independently CH, N, NH, O or S, and $X^3$ and $X^4$ independently represents N or C, but excluding compounds in which one of $X^2$ and $X^5$ is N and the other is NH and $X^3$ and $X^4$ are both C. Examples of suitable ring systems include furyl, imidazol-4 (5)-yl, oxadiazolyl, oxazolyl, pyrazolyl, pyrrolyl, thiazolyl, thienyl and triazolyl.

One of $R^1$ and $R^2$ may particularly represent optionally substituted azaheteroaryl such as optionally substituted pyridyl, pyrimidinyl, quinolinyl, isoquinolinyl, quinazolinyl, imidazolyl or benzimidazolyl (for example optionally substituted 4-pyridyl, 4-pyrimidinyl, 4-quinolinyl, 6-isoquinolinyl, 4-quinazolinyl, 1-imidazolyl or 1-benzimidazolyl) and the other may particularly represent optionally substituted phenyl. When $R^1$ or $R^2$ represents optionally substituted azaheteroaryl such as 2-substituted 4-pyridyl or 2-substituted 4-pyrimidinyl, preferred substituents include $C_{1-4}$alkyl (especially methyl), —$NY^1Y^2$ (especially where at least one of $Y^1$ and $Y^2$ is hydrogen) or —$OR^{11}$ (especially where $R^{11}$ is cycloalkyl). When $R^1$ or $R^2$ represents optionally substituted phenyl, 4-halophenyl (e.g. 4-fluorophenyl) is preferred.

$R^3$ may also particularly represent —$NY^1Y^2$, where $Y^1$ and $Y^2$ are as defined hereinbefore, especially where $Y^1$ and $Y^2$ are hydrogen.

$R^3$ may also particularly represent —$N(R^7)$—$C(=Z)$-$R^8$, in which Z, $R^7$ and $R^8$ are as defined hereinbefore, especially where Z is oxygen, $R^7$ is hydrogen and $R^8$ is alkyl (especially methyl), aryl (e.g. substituted or more preferably, unsubstituted phenyl) or heteroaryl.

$R^3$ may also particularly represent —$N(R^7)$—$C(=Z)$-$L^2$-$R^9$, in which Z, $L^2$, $R^7$ and $R^9$ are as defined hereinbefore, especially where Z is oxygen, $L^2$ is methylene, $R^7$ is hydrogen, and $R^9$ is aryl (e.g. substituted or more preferably, unsubstituted phenyl) or heteroaryl.

$R^3$ may also particularly represent —$C(=Z)$-$NY^1Y^2$, in which Z is as defined hereinbefore, especially oxygen, and $Y^1$ and $Y^2$ are as defined hereinbefore, especially where $Y^1$ and $Y^2$ are hydrogen or where $Y^1$ is hydrogen and $Y^2$ is aryl, arylalkyl, heteroaryl or heteroarylalkyl.

$R^3$ may also particularly represent —$C(=Z)$-$NY^1Y^2$, in which Z is as defined hereinbefore, especially oxygen, and the group —$NY^1Y^2$ forms a 5-7 membered cyclic amine [which may optionally contain a further heteroatom selected from O, S or $NY^5$ (where $Y^5$ is as defined hereinbefore)], preferably a 5-7 membered cyclic amine optionally containing oxygen, especially a morpholine ring.

$R^3$ may also particularly represent —$C(=Z)$-$OR^{10}$, in which Z and $R^{10}$ are as defined hereinbefore, especially where Z is oxygen and $R^{10}$ is $C_{1-4}$alkyl, preferably methyl.

$R^3$ may also particularly represent alkyl, especially methyl.

$R^3$ may also particularly represent a group -$L^1$-$R^6$ where $L^1$ is $C_{1-6}$alkylene, especially methylene, and $R^6$ is hydroxy.

$R^3$ may also particularly represent a group -$L^1$-$R^6$ where $L^1$ is $C_{1-6}$alkylene, especially methylene, and $R^6$ is —$N(R^7)$—$C(=Z)$—$R^8$, in which Z, $R^7$ and $R^8$ are as defined hereinbefore, especially where Z is oxygen, $R^7$ is hydrogen and $R^8$ is alkyl, aryl or heteroaryl.

$R^3$ may also particularly represent a group -$L^1$-$R^6$ where $L^1$ is $C_{1-6}$alkylene, especially methylene, and $R^6$ is —N($R^7$)—C(=Z)-$L^2$-$R^9$, in which Z, $L^2$, $R^7$, $R^8$ and $R^9$ are as defined hereinbefore, especially where Z is oxygen, $L^2$ is $C_{1-6}$alkylene, especially methylene, $R^7$ is hydrogen and $R^9$ is aryl or heteroaryl.

$R^3$ may also particularly represent a group -$L^1$-$R^6$ where $L^1$ is $C_{1-6}$alkylene, especially methylene, and $R^6$ is —NHC(=Z)-NH—$R^8$, in which Z and $R^8$ are as defined hereinbefore, especially where $R^8$ is alkyl, aryl or heteroaryl.

$R^3$ may also particularly represent a group -$L^1$-$R^6$ where $L^1$ is $C_{1-6}$alkylene, especially methylene, and $R^6$ is —NH—C(=Z)—NH-$L^2$-$R^9$, in which Z, $L^2$ and $R^9$ are as defined hereinbefore, especially where $L^2$ is methylene and $R^9$ is aryl or heteroaryl.

$R^3$ may also particularly represent a group -$L^1$-$R^6$ where $L^1$ is $C_{1-6}$alkylene, especially $C_{1-3}$alkylene, preferably methylene, and $R^6$ is —N$Y^1Y^2$, where $Y^1$ and $Y^2$ are as defined hereinbefore, especially where $Y^1$ and $Y^2$ are hydrogen.

$R^3$ may also particularly represent a group -$L^1$-$R^6$ where $L^1$ is $C_{1-6}$alkylene, especially methylene or ethylene, and $R^6$ is aryl or heteroaryl.

$R^3$ may also particularly represent a group -$L^1$-$R^6$ where $L^1$ is $C_{1-6}$alkylene, especially methylene, and $R^6$ is —N($R^7$)—$SO_2$—$R^8$, in which $R^7$ and $R^8$ are as defined hereinbefore, especially where $R^7$ is hydrogen and $R^8$ is alkyl, aryl or heteroaryl.

$R^3$ may also particularly represent a group -$L^1$-$R^6$ where $L^1$ is $C_{1-6}$alkylene, especially methylene, and $R^6$ is —N($R^7$)—$SO_2$-$L^2$-$R^8$, in which $L^2$, $R^7$ and $R^8$ are as defined hereinbefore, especially where $L^2$ is methylene, $R^7$ is hydrogen and $R^8$ is alkyl, aryl or heteroaryl.

$R^4$ may particularly represent hydrogen or $C_{1-4}$alkyl, especially methyl.

$R^3$ and $R^4$ are preferably attached to the same ring carbon atom.

$R^3$ and $R^4$ when attached to the same ring carbon atom, may also preferably form with the said carbon atom a group C=$CH_2$ or a 5-7 membered cyclic ether such as tetrahydrofuran-2-yl or perhydropyran-2-yl.

$R^5$ may particularly represent hydrogen or $C_{1-4}$alkyl, especially hydrogen.

m is preferably an integer 1.

The ring

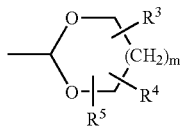

is preferably

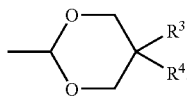

It is to be understood that this invention covers all appropriate combinations of the particular and preferred groupings referred to herein.

A particular group of compounds of the invention are compounds of formula (Ia)

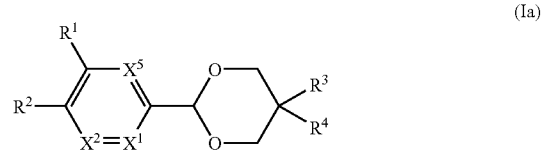

(Ia)

in which $R^3$, $R^4$, $X^1$, $X^2$ and $X^5$ are as hereinbefore defined, one of $R^1$ and $R^2$ is 4-pyridyl and the other is 4-fluorophenyl, and N-oxides thereof, and their prodrugs; and pharmaceutically acceptable salts and solvates (e.g. hydrates) of compounds of formula (Ia) and N-oxides thereof, and their prodrugs.

A further particular group of compounds of the invention are compounds of formula (Ib)

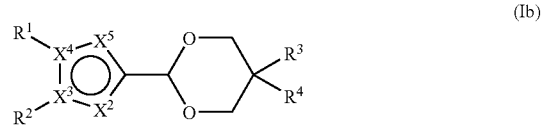

(Ib)

in which $R^3$, $R^4$, $X^2$, $X^3$, $X^4$ and $X^5$ are as hereinbefore defined, one of $R^1$ and $R^2$ is 4-pyridyl and the other is 4-fluorophenyl, and N-oxides thereof, and their prodrugs; and pharmaceutically acceptable salts and solvates (e.g. hydrates) of compounds of formula (Ib) and N-oxides thereof, and their prodrugs.

A further particular group of compounds of the invention are compounds of formula (Ic)

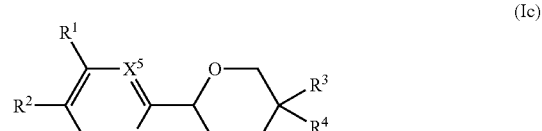

(Ic)

in which $R^3$, $R^4$, $X^1$, $X^2$ and $X^5$ are as hereinbefore defined, one of $R^1$ and $R^2$ is 4-fluorophenyl and the other is

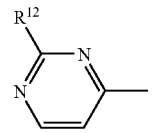

in which $R^{12}$ is $R^{11}Z^2$- or $Y^1Y^2N$— (wherein $R^{11}$, $Y^1$, $Y^2$ and $Z^2$ are as hereinbefore defined), and N-oxides thereof, and their prodrugs; and pharmaceutically acceptable salts and solvates (e.g. hydrates) of compounds of formula (Ic) and N-oxides thereof, and their prodrugs.

A further particular group of compounds of the invention are compounds of formula (Id)

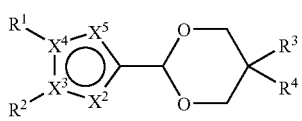

in which $R^3$, $R^4$, $X^2$, $X^3$, $X^4$ and $X^5$ are as hereinbefore defined, one of $R^1$ and $R^2$ is 4-fluorophenyl and the other is

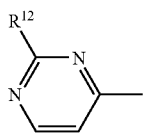

in which $R^{12}$ is $R^{11}Z^2$- or $Y^1Y^2N$— (wherein $R^{11}$, $Y^1$, $Y^2$ and $Z^2$ are as hereinbefore defined), and N-oxides thereof, and their prodrugs; and pharmaceutically acceptable salts and solvates (e.g. hydrates) of compounds of formula (Id) and N-oxides thereof, and their prodrugs.

Preferred compounds of the invention are those of formula (Ia), (Ib), (Ic) or (Id) in which $R^3$ is $C_{1-4}$alkyl (e.g. methyl) and $R^4$ represents $C_{1-4}$alkyl (e.g. methyl).

Further preferred compounds of the invention are those of formula (Ia), (Ib), (Ic) or (Id) in which $R^3$ is —C(=O)—$NY^1Y^2$ where $Y^1$ and $Y^2$ are as defined hereinbefore, especially (i) where $Y^1$ is hydrogen and $Y^2$ is alkyl or cycloalkyl, for example —C(=O)—$NHCH_2CH_2CH_3$ or

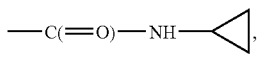

or (ii) where the group —$NY^1Y^2$ forms a 5-7 membered cyclic amine containing a further heteroatom selected from O or $NY^5$ (where $Y^5$ is H or alkyl), for example

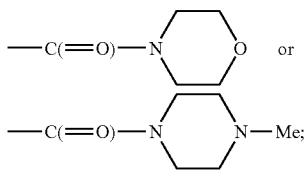

and $R^4$ represents $C_{1-4}$alkyl (e.g. methyl).

Within formula (Ic) or (Id) therein $R^{12}$ is preferably —$NY^1Y^2$ where $Y^1$ and $Y^2$ are as hereinbefore defined, especially where $Y^1$ is hydrogen and $Y^2$ is cycloalkyl or $C_{2-6}$alkyl substituted by $C_{1-4}$alkoxy, for example

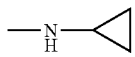

or —$NHCH_2CH_2OCH_3$.

A particular group of compounds of the invention are those selected from the following:
4-[5-(5,5-dimethyl-[1,3]dioxan-2-yl)-2-(4-fluoro-phenyl)-2H-pyrazol-3-yl]-pyridine;
4-[5-(5,5-dimethyl-[1,3]dioxan-2-yl)-2-(4-fluoro-phenyl)-2H-[1,2,4]triazol-3-yl]-pyridine;
4-[2-(5,5-dimethyl-[1,3]dioxan-2-yl)-5-(4-fluoro-phenyl)-oxazol-4-yl]-pyridine;
4-[2-(5,5-dimethyl-[1,3]dioxan-2-yl)-4-(4-fluoro-phenyl)-oxazol-5-yl]-pyridine;
{2-[1-(4-fluoro-phenyl)-5-pyridin-4-yl-4H-pyrazol-3-yl]-5-methyl-[1,3]dioxan-5-yl}-morpholin-4-yl-methanone;
{2-[1-(4-fluoro-phenyl)-5-pyridin-4-yl-1H-[1,2,4]triazol-3-yl]-5-methyl-[1,3]dioxan-5-yl}-morpholin-4-yl-methanone;
{2-[5-(4-fluoro-phenyl)-4-pyridin-4-yl-oxazol-2-yl]-5-methyl-[1,3]dioxan-5-yl}-morpholin-4-yl-methanone;
{2-[4-(4-fluoro-phenyl)-5-pyridin-4-yl-oxazol-2-yl]-5-methyl-[1,3]dioxan-5-yl}-morpholin-4-yl-methanone;
cyclopropyl-{4-[5-(5,5-dimethyl-[1,3]dioxan-2-yl)-2-(4-fluoro-phenyl)-4H-pyrazol-3-yl]-pyrimidin-2-yl}-amine;
cyclopropyl-{4-[5-(5,5-dimethyl-[1,3]dioxan-2-yl)-2-(4-fluoro-phenyl)-2H-[1,2,4]triazol-3-yl]-pyrimidin-2-yl}-amine;
cyclopropyl-{4-[2-(5,5-dimethyl-[1,3]dioxan-2-yl)-5-(4-fluoro-phenyl)-oxazol-4-yl ]-pyrimidin-2-yl}-amine;
cyclopropyl-{4-[2-(5,5-dimethyl-[1,3]dioxan-2-yl)-4-(4-fluoro-phenyl)-oxazol-5-yl ]-pyrimidin-2-yl}-amine;
2-{1-(4-fluoro-phenyl)-5-[2-(2-methoxy-ethylamino)-pyrimidin-4-yl]-1H-pyrazol-3-yl}-5-methyl-[1,3]dioxane-5-carboxylic acid propylamide;
2-{1-(4-fluoro-phenyl)-5-[2-(2-methoxy-ethylamino)-pyrimidin-4-yl]-1H-[1,2,4]triazol-13-yl]-5-methyl-[1,3]dioxane-5-carboxylic acid propylamide;
2-{5-(4-fluoro-phenyl)-4-[2-(2-methoxy-ethylamino)-pyrimidin-4-yl]-oxazol-2-yl}-5-methyl-[1,3]dioxane-5-carboxylic acid propylamide;
2-{4-(4-fluoro-phenyl)-5-[2-(2-methoxy-ethylamino)-pyrimidin-4-yl]-oxazol-2-yl}-5-methyl-[1,3]dioxane-5-carboxylic acid propylamide;
2-[1-(4-fluoro-phenyl)-5-(2-propylamino-pyrimidin-4-yl)-1H-pyrazol-3-yl]-5-methyl-[1,3]dioxane-5-carboxylic acid cyclopropylamide;
2-[1-(4-fluoro-phenyl)-5-(2-propylamino-pyrimidin-4-yl)-1H-[1,2,4]triazol-3-yl]-5-methyl-[1,3]dioxane-5-carboxylic acid cyclopropylamide;
2-[5-(4-fluoro-phenyl)-4-(2-propylamino-pyrimidin-4-yl)-oxazol-2-yl]-5-methyl-[1,3]dioxane-5-carboxylic acid cyclopropylamide;
2-[4-(4-fluoro-phenyl)-5-(2-propylamino-pyrimidin-4-yl)-oxazol-2-yl]-5-methyl-[1,31dioxane-5-carboxylic acid cyclopropylamide;
{2-[5-[2-(cyclopropylmethyl-amino)-pyrimidin-4-yl]-1-(4-fluoro-phenyl)-1H-pyrazol-3-yl]-5-methyl-[1,3]dioxan-5-yl}-(4-methyl-piperazin-1-yl)-methanone;
{2-[5-[2-(cyclopropylmethyl-amino)-pyrimidin-4-yl]-1-(4-fluoro-phenyl)-1H-[1,2,4]triazol-3-yl]-5-methyl-[1,3]dioxan-5-yl}-(4-methyl-piperazin-1-yl)-methanone;
{2-[4-[2-(cyclopropylmethyl-amino)-pyrimidin-4-yl]-5-(4-fluoro-phenyl)-oxazol-2-yl]-5-methyl-[1,3]dioxan-5-yl}-(4-methyl-piperazin-1-yl)-methanone;
{2-[5-[2-(cyclopropylmethyl-amino)-pyrimidin-4-yl]-4-(4-fluoro-phenyl)-oxazol-2-yl]-5-methyl-[1,3]dioxan-5-yl}-(4-methyl-piperazin-1-yl)-methanone;
{2-[5-(2-cyclopropylamino-pyrimidin-4-yl)-1-(4-fluoro-phenyl)-4H-pyrazol-3-yl]-5-methyl-[1,3]dioxan-5-yl}-morpholin-4-yl-methanone, trans-isomer;

{2-[5-(2-cyclopropylamino-pyrimidin-4-yl)-1-(4-fluoro-phenyl)-1H-[1,2,4]triazol-3-yl]-5-methyl-[1,3]dioxan-5-yl}-morpholin-4-yl-methanone;

{2-[4-(2-cyclopropylamino-pyrimidin-4-yl)-5-(4-fluoro-phenyl)-oxazol-2-yl]-5-methyl-[1,3]dioxan-5-yl}-morpholin-4-yl-methanone;

{2-[5-(2-cyclopropylamino-pyrimidin-4-yl)-4-(4-fluoro-phenyl)-oxazol-2-yl]-5-methyl-[1,3]dioxan-5-yl}-morpholin-4-yl-methanone;

and the corresponding N-oxides, and their prodrugs; and pharmaceutically acceptable salts and solvates (e.g. hydrates) of such compounds and their N-oxides and prodrugs.

The compounds of the invention exhibit useful pharmacological activity and accordingly are incorporated into pharmaceutical compositions and used in the treatment of patients suffering from certain medical disorders. The present invention thus provides, according to a further aspect, compounds of the invention and compositions containing compounds of the invention for use in therapy.

Compounds within the scope of the present invention are inhibitors of the generation of tumour necrosis factor (TNF), especially TNF-alpha, according to tests described in the literature and described in vitro and in vivo procedures hereinafter, and which tests results are believed to correlate to pharmacological activity in humans and other mammals. Thus, in a further embodiment, the present invention provides compounds of the invention and compositions containing compounds of the invention for use in the treatment of a patient suffering from, or subject to, conditions which can be ameliorated by the administration of an inhibitor of TNF, especially of TNF-alpha. For example, compounds of the present invention are useful in the treatment of joint inflammation, including arthritis, rheumatoid arthritis and other arthritic conditions such as rheumatoid spondylitis, gouty arthritis, traumatic arthritis, rubella arthritis, psoriatic arthritis and osteoarthritis. Additionally, the compounds are useful in the treatment of acute synovitis, tuberculosis, atherosclerosis, muscle degeneration, cachexia, Reiter's syndrome, endotoxaemia, sepsis, septic shock, endotoxic shock, gram negative sepsis, gout, toxic shock syndrome, chronic pulmonary inflammatory diseases including asthma and adult respiratory distress syndrome, silicosis, pulmonary sarcoidosis, bone resorption diseases, osteoporosis, restenosis, heart failure and myocardial ischaemic syndromes, cardiac and renal reperfusion injury, thrombosis, glomerularnephritis, graft vs. host reaction, allograft rejection and leprosy. Furthermore, the compounds are useful in the treatment of infections such as viral infections, for example HIV, cytomegalovirus (CMV), influenza, adenovirus and the Herpes group of viruses, parasitic infections, for example malaria such as cerebral malaria, and yeast and fungal infections, for example fungal meningitis; fever and myalgias due to infection; AIDS; AIDS related complex (ARC); cachexia secondary to infection or malignancy; cachexia secondary to acquired immune deficiency syndrome (AIDS) or to cancer; keloid and scar tissue formation; pyresis; diabetes; inflammatory bowel diseases such as Crohn's disease and ulcerative colitis; eczema; contact dermititis; psoriasis; sunburn and conjunctivitis.

Compounds of the invention are also useful in the treatment of diseases of, or injury to, the brain in which overproduction of TNF-alpha has been implicated, such as multiple sclerosis, Alzheimers disease, trauma, stroke and other ischaemic conditions.

Compounds of the invention may also be useful in inhibiting diseases associated with over-production of other pro-inflammatory cytokines, IL-1, IL-6 and IL-8.

A special embodiment of the therapeutic methods of the present invention is the treating of asthma.

Another special embodiment of the therapeutic methods of the present invention is the treating of joint inflammation.

According to a further feature of the invention there is provided a method for the treatment of a human or animal patient suffering from, or subject to, conditions which can be ameliorated by the administration of an inhibitor of TNF, especially TNF-alpha, for example conditions as hereinbefore described, which comprises the administration to the patient of an effective amount of compound of the invention or a composition containing a compound of the invention.

"Effective amount" is meant to describe an amount of compound of the present invention effective in inhibiting TNF and thus producing the desired therapeutic effect.

References herein to treatment should be understood to include prophylactic therapy as well as treatment of established conditions.

The present invention also includes within its scope pharmaceutical compositions comprising at least one of the compounds of the invention in association with a pharmaceutically acceptable carrier or excipient.

Compounds of the invention may be administered by any suitable means. In practice compounds of the present invention may generally be administered parenterally, topically, rectally, orally or by inhalation, especially by the oral route.

Compositions according to the invention may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations. The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

For topical administration, gels (water or alcohol based), creams or ointments containing compounds of the invention may be used. Compounds of the invention may also be incorporated in a gel or matrix base for application in a patch, which would allow a controlled release of compound through the transdermal barrier.

For administration by inhalation compounds of the invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of the invention.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The compounds according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day.

Compounds of the invention may be prepared by the application or adaptation of known methods, by which is meant methods used heretofore or described in the literature, for example those described by R. C. Larock in Comprehensive Organic Transformations, VCH publishers, 1989 and methods similar to those described in EP424195 and EP506437.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Thus, for example, compounds of formula (I), wherein Het, $R^3$, $R^4$, $R^5$ and m are as defined in formula (I), may be prepared by reaction of a compound of formula (II):—

Het-$R^{13}$ (II)

wherein Het is as just hereinbefore defined and $R^{13}$ is —CHO or —CH(OC$_{1-4}$alkyl)$_2$ [e.g. —CH(OMe)$_2$ or —CH(OEt)$_2$] with a compound of formula (III):—

(III)

wherein $R^3$, $R^4$, $R^5$ and m are as just hereinbefore defined. The reaction may conveniently be carried out in the presence of an acid catalyst, such as pyridinium 4-toluene sulphonate or 4-toluene sulphonic acid, in an inert solvent, such as toluene, at reflux temperature, with azeotropic removal of the water formed in the reaction.

As another example, compounds of formula (I), in which within Het $R^1$ represents

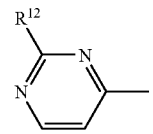

wherein $R^{12}$ is $Y^4Y^5N$— [in which $Y^4$ and $Y^5$ are as defined in formula (I)], may be prepared by reaction of a compound of formula (IV):—

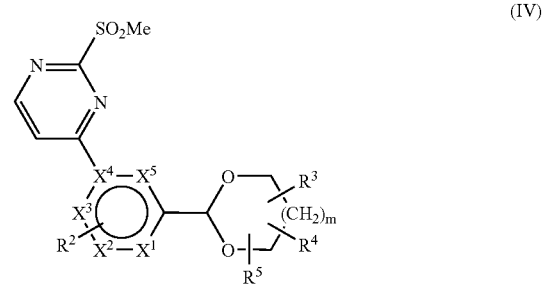

(IV)

wherein $R^2$, $R^4$, $R^5$, $X^1$, $X^2$, $X^3$, $X^4$ and $X^5$ are as defined in formula (I), with an amine of formula HN$Y^4Y^5$ wherein $Y^4$ and $Y^5$ are as just hereinbefore defined. The reaction may conveniently be carried out in an inert solvent such as dimethylformamide at a temperature up to about 100° C. When $Y^5$ is hydrogen the reaction may be conveniently carried out in a sealed vessel. When $Y^5$ is aryl, for example phenyl, the reaction may be conveniently carried out with the lithio-anion of the amine.

Alternatively, compounds of formula (I), in which within Het $R^1$ represents

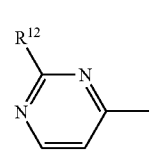

wherein $R^{12}$ is $Y^4Y^5N$—[in which $Y^4$ and $Y^5$ are as defined in formula (I)], may be prepare (i) treating Merrifield resin (chloromethylated styrene/divinylbenzene copolymer) with potassium thioacetate in an inert solvent, such as dimethylformamide, at a temperature at about room temperature, to give Resin A;

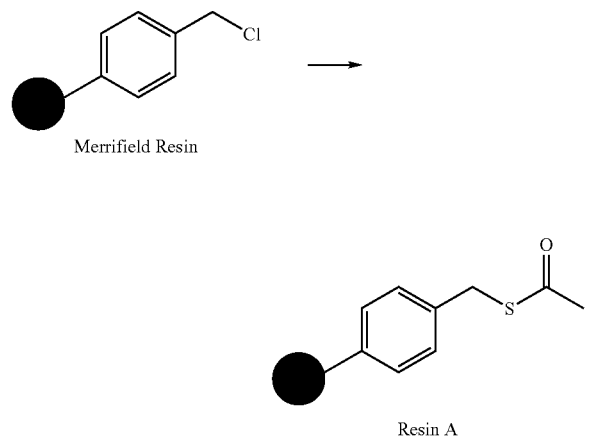

Merrifield Resin

Resin A where

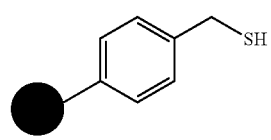

represents the polymeric core comprising polystyrene crosslinked with 1% to 2% divinylbenzene.

(ii) reacting Resin A with lithium borohydride in an inert solvent, such as tetrahydrofuran, and at a temperature at about room temperature, to give Resin B;

Resin B (iii) reacting Resin B with an alkali metal hydride, such as sodium hydride, in an inert solvent, such as dimethylformamide, at a temperature at about room temperature, followed by treatment with compounds of formula (IV), at a temperature from about room temperature to about 80° C., to give Resin C

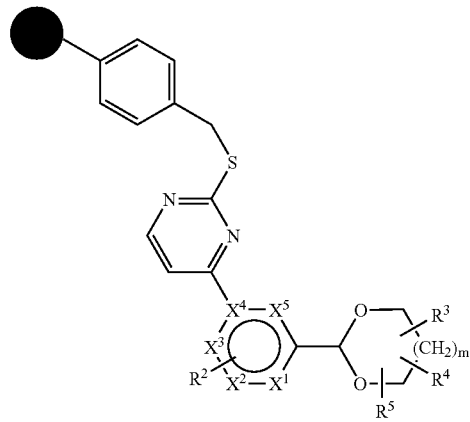

Resin C in which $R^2$, $R^3$, $R^4$, $R^5$ and m are as defined in (IV) above; followed by appropriate functional group interconversions, for example those described hereinafter:

(iv) reacting Resin C, in which $R^2$, $R^3$, $R^4$, $R^5$ and m are as just hereinbefore defined, with m-chloroperoxybenzoic acid, in an inert solvent or preferably in a mixture of inert solvents, such as a mixture of dichloromethane and methanol, to give resin D, in which $R^2$, $R^3$, $R^4$, $R^5$ and m are as just hereinbefore defined;

Resin D (v) reacting Resin D, wherein $R^2$, $R^3$, $R^4$, $R^5$ and m are as just hereinbefore defined, with an amine of formula $HNY^4Y^5$, wherein $Y^4$ and $Y^5$ are as defined in formula (I), in an inert solvent, such as dimethoxyethane, and at a temperature at about 70° C.

As another example, compounds of formula (I) wherein $R^3$, $R^4$, $R^5$ and m are as hereinbefore defined in formula (I) and within Het $R^1$ represents

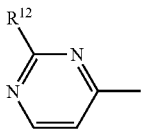

[where $R^{12}$ is a —$OR^{11}$ group in which $R^{11}$ is as defined in formula (I)] may be prepared by treating a compound of formula (IV) as defined above, with an appropriately substituted alcohol of formula $R^{11}OH$ (in which $R^{11}$ is as defined in formula (I)). The reaction may conveniently be carried out in the presence of an alkali metal hydride, such as sodium hydride, in a mixture of inert solvents, for example tetrahydrofuran and dimethylformamide, and at a temperature at about room temperature.

Alternatively compounds of formula (I) wherein $R^3$, $R^4$, $R^5$ and m are as defined in formula (I) and within Het $R^1$ represents

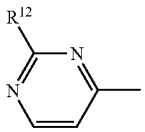

[where $R^{12}$ is a —$OR^{11}$ or —$SR^{11}$ group in which $R^{11}$ is as defined in formula (I)] may be prepared by reacting Resin D, wherein as defined above, with a compound of formula $R^{11}OH$ or $R^{11}SH$ (in which $R^{11}$ is as defined in formula (I)), in the presence of an alkali metal hydride, such as sodium hydride, in an inert solvent, such as dimethylformamide, and at a temperature from about room temperature to about 80° C.

According to a further feature of the present invention, compounds of the invention may be prepared by interconversion of other compounds of the invention.

As another example of the interconversion process, compounds of formula (I) in which $R^3$ contains a —$NH_2$ group may be prepared by reacting a compound of formula (I) in which $R^3$ contains a —$NHC(=O)CF_3$ group with a base such as potassium or ammonium carbonate in methanol, or a mixture of methanol and water, at a temperature at about reflux temperature.

As another example of the interconversion process, compounds of formula (I) in which $R^3$ contains a —$N(R^7)$—$C(=O)$—$R^8$ or —$N(R^7)$—$C(=O)$-$L^2$-$R^9$ group (in which $R^7$, $R^8$, $R^9$ and $L^2$ are as defined in formula (I)), may be prepared by reacting a compound of formula (I) in which $R^3$ contains a —$NHR^7$ group (in which $R^7$ is as defined in formula (I)) with an appropriately substituted acid chloride Cl—$C(=O)$—$R^8$ or Cl—$C(=O)$-$L^2$-$R^9$ (in which $R^8$, $R^9$ and $L^2$ are as defined in formula (I)) in the presence of triethylamine in an inert solvent such as tetrahydrofuran and at a temperature at about room temperature.

As another example of the interconversion process, compounds of formula (I) in which $R^3$ contains a —NH—C(=O)—$R^8$ or —NH—C(=O)-$L^2$-$R^9$ group (in which $R^8$, $R^9$ and $L^2$ are as defined in formula (I)) may be prepared by reacting a compound of formula (I) in which $R^3$ contains a —$NH_2$ group, with an appropriately substituted acid HO—C(=O)—$R^8$ or HO—C(=O)-$L^2$-$R^9$ (in which $R^8$, $R^9$ and $L^2$ are as just hereinbefore defined) respectively, in the presence of O-(7-azabenzotriazol-1-yl)-1,1,3,3-tetramethyluronium hexafluorophosphate and diisopropylethylamine in dimethylformamide, at room temperature. Other standard peptide coupling procedures may be employed for the reaction, such as treatment with a carbodiimide, for example dicyclohexylcarbodiimide, in the presence of triethylamine, or treatment with 1-hydroxybenzotriazole and a carbodiimide, such as 1-(3-dimethylaminopropyl)-3-ethylcarbodiimide, in an inert solvent such as dimethylformamide and at a temperature at about room temperature.

As another example of the interconversion process, compounds of formula (I) in which $R^3$ contains a —NH—C(=O)—$R^8$ or a —NH—C(=O)-$L^2$-$R^9$ group (in which $R^8$, $R^9$ and $L^2$ are as just hereinbefore defined), may be prepared by reacting a compound of formula (I) in which $R^3$ contains a —$NH_2$ group, with the appropriately substituted acid anhydride $R^8$—C(=O)—O—C(=O)—$R^8$ or $R^9$-$L^2$-C(=O)—O—C(=O)-$L^2$-$R^9$ (in which $R^8$, $R^9$ and $L^2$ are as just hereinbefore defined) in the presence of triethylamine or pyridine, in an inert solvent, such as tetrahydrofuran, and at a temperature at about room temperature.

As another example of the interconversion process, compounds of formula (I) in which $R^3$ contains a —NH—C(=O)—NH—$R^8$ or —NH—C(=O)—NH-$L^2$-$R^9$ group (in which $R^8$, $R^9$ and $L^2$ are as just hereinbefore defined), may be prepared by reacting a compound of formula (I) in which $R^3$ contains a —$NH_2$ group, with the appropriately substituted isocyanate O=C=N—$R^8$ or O=C=N-$L^2$-$R^9$ (in which $R^8$, $R^9$ and $L^2$ are as just hereinbefore defined), in an inert solvent, such as tetrahydrofuran, and at a temperature at about room temperature.

As another example of the interconversion process, compounds of formula (I) in which $R^3$ contains a —NH—(C=S)—NH—$R^8$ or —NH—(C=S)—NH-$L^2$-$R^9$ group (in which $R^8$, $R^9$ and $L^2$ are as just hereinbefore defined), may prepared by reacting a compound of formula (I) in which $R^3$ contains a —$NH_2$ group, with an appropriately substituted isothiocyanate S=C=N—$R^8$ or S=C=N-$L^2$-$R^9$ (in which $R^8$, $R^9$ and $L^2$ are as just hereinbefore defined), in an inert solvent, such as tetrahydrofuran, and at a temperature at about reflux temperature.

As another example of the interconversion process, compounds of formula (I) in which $R^3$ contains a —$CO_2H$ group, may be prepared by hydrolysis of a corresponding compound of formula (I) in which $R^3$ contains a —$CO_2R^{14}$ group (in which $R^{14}$ is as hereinbefore defined). The hydrolysis may conveniently be carried out by alkaline hydrolysis using a base, such as an alkali metal hydroxide or carbonate, in the presence of an aqueous/organic solvent mixture, using organic solvents such as dioxan, tetrahydrofuran or methanol, at a temperature from about ambient to about reflux. The hydrolysis may also be carried out by acid hydrolysis using an inorganic acid, such as hydrochloric acid, in the presence of an aqueous/inert organic solvent mixture, using organic solvents such as dioxan or tetrahydrofuran, at a temperature from about 50° C. to about 80° C.

As another example of the interconversion process, compounds of formula (I) in which $R^3$ contains a —C(=O)—$NY^4Y^5$ group (in which $Y^4$ and $Y^5$ are as defined in formula (I)), may be prepared by reacting a compound of formula (I) in which $R^3$ contains a —$CO_2H$ group, with an appropriately substituted amine of formula $HNY^4Y^5$ (in which $Y^4$ and $Y^5$ are as just hereinbefore defined). The coupling reaction may conveniently be carried out in the presence of 1-hydroxybenzotriazole and a carbodiimide such as 1-(3-dimethylaminopropyl)-3-ethylcarbodiimide in an inert solvent such as dimethylformamide and at a temperature at about room temperature. Alternatively the reaction may be carried out by initial conversion of the acid of formula (I), wherein $R^3$ contains a —$CO_2H$ group, to the corresponding acid chloride (for example by reaction with thionyl chloride or oxalyl chloride at room temperature) followed by treatment with an appropriately substituted amine of formula $HNY^4Y^5$.

As another example of the interconversion process, compounds of formula (I) containing sulphoxide linkages may be prepared by the oxidation of a corresponding compound containing an —S— linkage. For example, the oxidation may conveniently be carried out by means of reaction with a peroxyacid, e.g. 3-chloroperbenzoic acid, preferably in an inert solvent, e.g. dichloromethane, preferably at or near room temperature, or alternatively by means of potassium hydrogen peroxomonosulphate in a medium such as aqueous methanol, buffered to about pH5, at temperatures between about 0° C. and room temperature. This latter method is preferred for compounds containing an acid-labile group.

As another example of the interconversion process, compounds of formula (I) containing sulphone linkages may be prepared by the oxidation of a corresponding compounds containing an —S— or sulphoxide linkage. For example, the oxidation may conveniently be carried out by means of reaction with a peroxyacid, e.g. 3-chloroperbenzoic acid, preferably in an inert solvent, e.g. dichloromethane, preferably at or near room temperature.

As another example of the interconversion process, compounds of formula (I) in which $R^3$ contains a —$N(R^7)$—$SO_2$—$R^8$ or —$N(R^7)$—$SO_2$-$L^2$-$R^9$ group (in which $R^7$, $R^8$, $R^9$ and $L^2$ are as defined in formula (I)), may be prepared from a corresponding compound of formula (I) in which $R^3$ contains a —$NH_2$ group by treatment with the appropriately substituted acid chloride Cl—$SO_2$—$R^8$ or Cl—$SO_2$-$L^2$-$R^9$ (in which $R^8$, $R^9$ and $L^2$ are as just hereinbefore defined), in the presence of a suitable base, such as triethylamine, in an inert solvent, such as tetrahydrofuran, and at a temperature at about room temperature.

It will be appreciated that compounds of the present invention may contain asymmetric centres. These asymmetric centres may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of formula (I) hereinabove. Such isomers can be separated from their mixtures, by the application or adaptation of known methods, for example chromatographic techniques and recrystallisation techniques, or they are separately prepared from the appropriate isomers of their intermediates. Additionally, in situations where tautomers of the compounds of formula (I) are possible, the present invention is intended to include all tautomeric forms of the compounds.

According to a further feature of the invention, acid addition salts of the compounds of this invention may be prepared by reaction of the free base with the appropriate acid, by the application or adaptation of known methods. For example, the acid addition salts of the compounds of this invention may be prepared either by dissolving the free base in water or an aqueous alcohol solution or other suitable solvents containing the appropriate acid and isolating the salt by evaporating the solution, or by reacting the free base and acid in an organic solvent, such as tetrahydrofuran, in which case the salt separates directly or can be obtained by concentration of the solution.

Compounds of this invention can be regenerated from their acid addition salts by the application or adaptation of known methods. For example, parent compounds of the invention can be regenerated from their acid addition salts by treatment with an alkali, e.g. aqueous sodium bicarbonate solution or aqueous ammonia solution.

According to a further feature of the invention, base addition salts of the compounds of this invention may be prepared by reaction of the free acid with the appropriate base, by the application or adaptation of known methods. For example, the base addition salts of the compounds of this invention may be prepared either by dissolving the free acid in water or aqueous alcohol solution or other suitable solvents containing the appropriate base and isolating the salt by evaporating the solution, or by reacting the free acid and base in an organic solvent, in which case the salt separates directly or can be obtained by concentration of the solution.

Compounds of this invention can be regenerated from their base addition salts by the application or adaptation of known methods. For example, parent compounds of the invention can be regenerated from their base addition salts by treatment with an acid, e.g. hydrochloric acid.

Compounds of the present invention may be conveniently prepared, or formed during the process of the invention, as solvates (e.g. hydrates). Hydrates of compounds of the present invention may be conveniently prepared by recrystallisation from water.

The starting materials and intermediates may be prepared by the application or adaptation of known methods, for example methods as described in the Reference Examples or their obvious chemical equivalents.

Intermediates of formula (II) wherein Het is as defined in formula (I) above and $R^{13}$ is —$CH(OC_{1-4}alkyl)_2$ may be prepared by reacting a compound of formula (II) wherein Het is as just hereinbefore defined and $R^{13}$ is —CHO with a trialkylorthoformate, such as trimethyl- or triethylorthoformate in the presence of an acid catalyst, such as 4-toluene sulphonic acid, in methanol at reflux temperature.

Intermediates of formula (II) wherein Het is

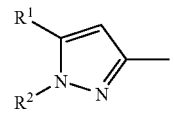

[in which $R^1$ and $R^2$ are as defined in formula (I)] and $R^{13}$ is —$CH(OMe)_2$ may be prepared by reacting a compound of formula (1):—

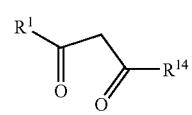

(1)

wherein $R^1$ is as just hereinbefore defined and $R^{14}$ is —CH(OMe)$_2$, with a hydrazine of formula (2):—

$R^2$—NH—$NH_2$ (2)

wherein $R^2$ is as just hereinbefore defined, in ethanol at reflux temperature.

Compounds of formula (1) wherein $R^1$ is as just hereinbefore defined and $R^{14}$ is —$CH(OMe)_2$ may be prepared by reacting a compound of formula (3):—

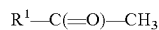

$R^1$—C(=O)—$CH_3$ (3)

wherein $R^1$ is as just hereinbefore defined, with methyl dimethoxyacetate in the presence of a suitable base, such as lithium bis (trimethylsilyl)amide, in an inert solvent, such as tetrahydrofuran, and at a temperature from about −40° C. to about room temperature. This reaction is particularly suitable for the preparation of compounds of formula (1) where $R^1$ is pyridyl.

Intermediates of formula (II) wherein Het is as defined in formula (I) and $R^{13}$ is —CHO may be prepared by ozonolysis of a corresponding alkene of formula (4):—

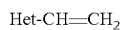    (4)

wherein Het is as just hereinbefore defined using standard methods such as those described in Comprehensive Organic Transformations, R. C. Larock, page 595. This method is particularly suitable for the preparation of intermediates of formula (II) wherein Het is

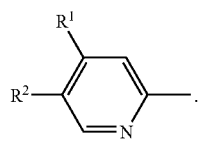

Alkenes of formula (4) wherein Het is

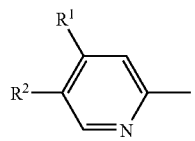

[in which $R^1$ and $R^2$ are as defined in formula (I)] may be prepared by adaptation of the methodology described by Ciufolini, M A et al., J. Am. Chem. Soc. 1996, 118(48), 12082-12089.

Intermediates of formula (II) wherein Het is as defined in formula (I) and $R^{13}$ is —CHO may also be prepared by oxidation of a compound of formula (5):—

    (5)

wherein Het is as just hereinbefore defined using standard methods such as those described in Comprehensive Organic Transformations, R. C. Larock, page 591.

Compounds of formula (5) wherein Het is

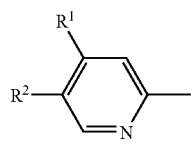

[in which $R^1$ and $R^2$ are as defined in formula (I)] may be prepared by application or adaptation of the methodology described by Reid W and Erle H-E, Chem. Ber. 112,640-647.

Intermediates of formula (II) wherein Het is as defined in formula (I) and $R^{13}$ is —CHO may also be prepared by reduction of a corresponding ester of formula (6):—

    (6)

wherein Het is as defined immediately hereinabove and $R^{15}$ is alkyl, preferably methyl or ethyl, using standard methodologies (e.g. those described in Comprehensive Organic Transformations, R. C. Larock, page 621).

Esters of formula (6) wherein Het is

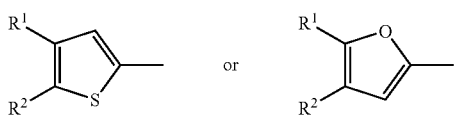

[in which $R^1$ and $R^2$ are as defined in formula (I)] and $R^{15}$ is alkyl may be prepared by the application or adaptation of the methods described in the specification of European Patent Application No. EP 728755.

Esters of formula (6) wherein Het is

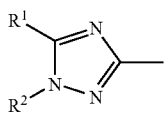

[in which $R^1$ and $R^2$ are as defined in formula (I)] and $R^{15}$ is alkyl may be prepared by the application or adaptation of methods described by Bruche, Luca et al., Synthesis, 1985, 3, 304-5.

Esters of formula (6) wherein Het is

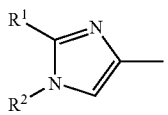

[in which $R^1$ and $R^2$ are as defined in formula (I)] and $R^{15}$ is alkyl may be prepared by the application or adaptation of methods described by I. K. Khanna et al., J.Med.Chem., 1997, 40, pages 1634-1647.

Esters of formula (6) wherein Het is

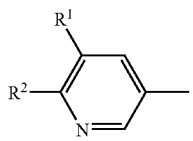

[in which $R^1$ and $R^2$ are as defined in formula (I)] and $R^{15}$ is alkyl may be prepared by the application or adaptation of methods described in the specification of International Patent Application Publication No. WO 98/03484.

Esters of formula (6) wherein Het is

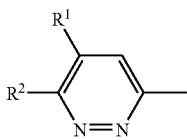

[in which $R^1$ and $R^2$ are as defined in formula (I)] and $R^{15}$ is methyl may be prepared by methoxycarbonylation of a corresponding pyridazine-6-trifluoromethanesulphonate (7):—

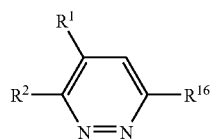 (7)

wherein $R^1$ and $R^2$ are as just hereinbefore defined and $R^{16}$ is —$OSO_2CF_3$ by the application or adaptation of the procedure described by Rhor, M et al., Heterocycles, 1996, 43, 1459-1464.

Intermediates of formula (II) wherein Het

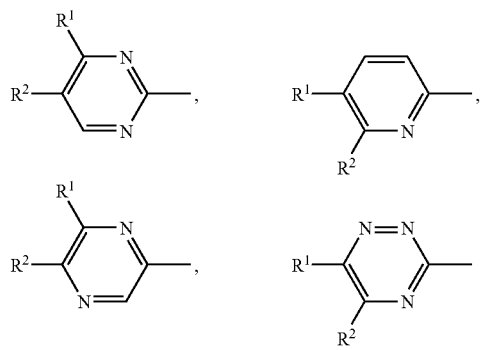

[in which $R^1$ and $R^2$ are as defined in formula (I)] and $R^{13}$ is —CHO may be prepared by the application or adaptation of methods described in the specification of International Patent Application No. WO92/02513.

Intermediates of formula (II) wherein Het is as defined in formula (I) and $R^{13}$ is —CHO may also be prepared by oxidation of compounds of formula (8):—

Het-CH$_2$OH (8)

wherein Het is as defined immediately hereinabove using standard methodologies, for example those described in Comprehensive Organic Transformations, R. C. Larock, page 604.

Compounds of formula (8) wherein Het is

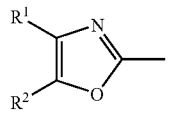

[in which $R^1$ and $R^2$ are as defined in formula (I)] may be prepared by adaptation of the methods described by Norman, B. H. in U.S. Pat. No. 5,719,163.

Intermediates of formula (I) wherein Het is

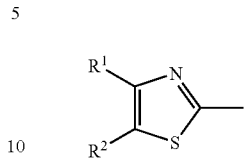

[in which $R^1$ and $R^2$ are as defined in formula (I)] and $R^{13}$ is —CHO may be prepared by adaptation of the methods described by V.Cecchetti et al., Bioorg. Med. Chem., 1994, 2, pages 799-806.

4-Formylimidazoles of formula (II) wherein Het is

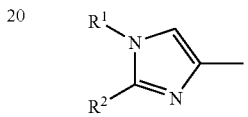

[in which $R^1$ and $R^2$ are as defined in formula (I)] and $R^{13}$ is —CHO may be prepared by adaptation of the methods described by C. Gonczi, J. Org. Chem., 1981, 46, pages 608-610.

4-Formylimidazoles of formula (II) wherein Het is

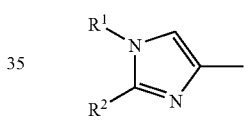

[in which $R^1$ and $R^2$ are as defined in formula (I)] and $R^{13}$ is —CHO may also be prepared by the application or adaptation of methods described by I. K. Khanna et al., J.Med.Chem., 1997, 40, pages 1634-1647.

Intermediates of formula (II) wherein Het is as defined in formula (I) and $R^{13}$ is —CHO may be prepared by Vilsmeyer formylation of the corresponding compounds formula (9):—

Het-H (9)

wherein Het is as defined immediately hereinabove. The formylation may conveniently be carried out by: (i) treatment with lithium bis(trimethylsilyl)amide in an inert atmosphere and in an inert solvent, such as tetrahydrofuran, at a temperature at about −10° C.; (ii) reaction of the resulting anion with N-formylmorpholine.

Pyrrole derivatives of formula (9) wherein Het is

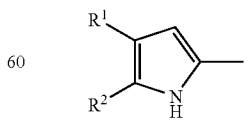

[in which $R^1$ and $R^2$ are as defined in formula (I)] may be prepared by adaptation of the methods described by Katritzky, A R, Tetrahedron, 1995, 51, 13271-6.

Oxazole derivatives of formula (9) wherein Het is

[structure: oxazole with R¹ at 5-position, R² at 4-position, methyl at 2-position]

[in which R¹ and R² are as defined in formula (I)] may be prepared by reaction of compounds of formula (10):—

[structure (10): R¹-CHBr-C(=O)-R²]

wherein R¹ and R² are as just hereinbefore defined, with urea and formic acid in an inert solvent, such as acetonitrile, in the presence of triethylamine and at a temperature at about reflux temperature.

Compounds of formula (10) wherein R¹ and R² are as defined in formula (I) may be prepared by reaction of compounds of formula (11):

[structure (11): R¹-CH₂-C(=O)-R²]

wherein R¹ and R² are as just hereinbefore defined, with bromine in an inert solvent, such as dichloromethane and at a temperature at about room temperature.

Compounds of formula (11) wherein R¹ and R² are as defined in formula (I) may be prepared by the application or adaptation of the methods described in the specification of International Patent Application No. WO98/56788 for Reference Examples 9 and 11.

Oxazole derivatives of formula (9) wherein Het is

[structure: oxazole with R¹ at 4-position, R² at 5-position, methyl at 2-position]

[in which R¹ and R² are as defined in formula (I)] may be prepared by reaction of compounds of formula (12):

[structure (12): R¹-C(=N-OH)-C(=O)-R²]

wherein R¹ and R² are as just hereinbefore defined, with zinc in formic acid at a temperature at about reflux temperature.

Compounds of formula (12) wherein R¹ and R² are as defined in formula (I) may be prepared by reaction of compounds of formula (11) wherein R¹ and R² are as defined in formula (I) with sodium nitrite in water at a temperature at about 10° C.

Intermediates of formula (II) wherein Het is

[structure: triazole with R¹ and R², methyl group]

[in which R¹ and R² are as defined in formula (I)] and R¹³ is —CH(OEt)₂ may be prepared by reacting compounds of formula (13):—

[structure (13): R²-NH-N(H)-C(=NH)-CH(OEt)₂]

wherein R² is as just hereinbefore defined with acid halides of formula (14):—

R¹—C(=O)—X⁶                                (14)

wherein R¹ is as just hereinbefore defined and X⁶ is a halogen, preferably chlorine, atom in the presence of a suitable base, such as triethylamine, in an inert solvent, such as dichloromethane, and at a temperature at about room temperature, followed by cyclisation of the resulting intermediate by heating at reflux temperature in toluene with azeotropic removal of water.

Compounds of formula (13) wherein R² is as defined in formula (I) may be prepared by reaction of methyl diethoxyacetimidate (prepared according to the procedure of Schaefer et.al. J.Org.Chem., 1961, 26, pages 412-418) with hydrazines of formula (15):—

R²—NH—NH₂.HCl                              (15)

wherein R² is as just hereinbefore defined at a temperature at about room temperature.

Intermediate 1,3-propanediols of formula (III), wherein R³ is an azidomethyl group, R⁴ is a methyl group, R⁵ is hydrogen and m is 1, and where both R³ and R⁴ are attached in the 2-position, may be prepared by reacting 5-azidomethyl-2,5-dimethyl-1,3-dioxane (prepared according to the procedure in J.Org.Chem., 1992, 57, page 6080) with a mineral acid, for example hydrochloric acid, in an aqueous organic solvent mixture such as tetrahydrofuran and water, at reflux temperature.

Intermediate 1,3-propanediols of formula (III), wherein R³ is an —NHC(=O)CF₃ group, R⁴ is a methyl group, R⁵ is hydrogen and m is 1, and where both R³ and R⁴ are attached in the 2-position, may be prepared by reacting 2-amino-2-methyl-1,3-propanediol with trifluoroacetic acid in the presence of a base, such as potassium carbonate, in an inert solvent, such as dimethylformamide, and at a temperature at about room temperature.

Intermediate 1,3-propanediols of formula (III), wherein R³ is a —C(=O)—NY⁴Y⁵ group (in which Y⁴ and Y⁵ are as defined in formula (I) above), R⁴ is a methyl group, R⁵ is hydrogen and m is 1, and where both $R^3$ and $R^4$ are attached in the 2-position, may be prepared by reacting 2-carboxy-2-methyl-1,3-propanediol with an amine of formula $HNY^4Y^5$, wherein $Y^4$ and $Y^5$ are as just hereinbefore defined. The coupling may conveniently be carried out with a carbodiimide, such as dicyclohexylcarbodiimide, in the presence of 1-hydroxybenzotriazole and diisopropylethylamine, in an inert solvent, such as acetonitrile, and at a temperature from room temperature to about 55° C. Other standard peptide coupling procedures may be employed for the reaction, such as those described hereinbefore.

Resins of formula Resin C in which $R^2$, $R^4$, $R^5$ and m are as hereinbefore defined, and $R^3$ contains a —C(=O)—$NY^4Y^5$ group may be prepared from a corresponding Resin C, in which $R^2$, $R^4$, $R^5$ and m are as hereinbefore defined and $R^3$ contains a —C(=O)—$OR^{14}$ group (in which $R^{14}$ is alkyl, aryl or arylalkyl), by: (i) treatment with an alkali metal hydroxide, such as sodium hydroxide, in a mixture of water and a water miscible inert organic solvent, such as tetrahydrofuran, and at a temperature from about room temperature to about 70° C.; (ii) treatment of the resulting resin in which $R^3$ contains a —C(=O)—OH group with oxalyl chloride solution in an inert solvent, such as dichloromethane, at a temperature at about room temperature; (iii) treatment of the resulting resin in which $R^3$ contains a —C(=O)—Cl group with an amine of formula $HNY^4Y^5$ in an inert solvent, such as dichloromethane, at a temperature at about room temperature.

Resins of formula Resin C in which $R^2$, $R^4$, $R^5$ and m are as hereinbefore defined, and $R^3$ contains a —N($R^7$)—C(=O)—$R^8$ or —N($R^7$)—C(=O)-$L^2$-$R^9$ group (in which $R^7$, $R^8$, $R^9$ and $L^2$ are as hereinbefore defined), may be prepared from a corresponding Resin C, in which $R^2$, $R^4$, $R^5$ and m are as hereinbefore defined and $R^3$ contains a —$NH_2$ group by treatment with the appropriately substituted acid chloride Cl—C(=O)—$R^8$ or Cl—C(=O)-$L^2$-$R^9$ (in which $R^8$, $R^9$ and $L^2$ are as hereinbefore defined), in the presence of triethylamine, in an inert solvent, such as tetrahydrofuran, and at a temperature at about room temperature.

Resins of formula Resin C in which $R^2$, $R^4$, $R^5$ and m are as hereinbefore defined, and $R^3$ contains a —N($R^7$)—$SO_2$—$R^8$ or —N($R^7$)—$SO_2$-$L^2$-$R^9$ group (in which $R^7$, $R^8$, $R^9$ and $L^2$ are as hereinbefore defined), may be prepared from a corresponding Resin C, in which $R^2$, $R^4$, $R^5$ and m are as hereinbefore defined and $R^3$ contains a —$NH_2$ group by treatment with the appropriately substituted sulphonyl chloride Cl—$SO_2$—$R^8$ or Cl—$SO_2$-$L^2$-$R^9$ (in which $R^8$, $R^9$ and $L^2$ are as hereinbefore defined), in the presence of triethylamine, in an inert solvent, such as tetrahydrofuran, and at a temperature at about room temperature.

Compounds of formula (IV) may conveniently be prepared by means of reacting a compound of formula (16):

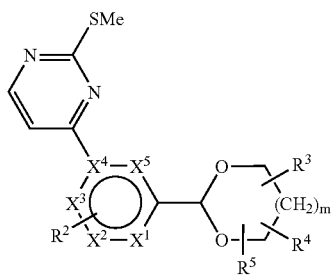

(16)

wherein $R^2$, $R^4$, $R^5$, $X^1$, $X^2$, $X^3$, $X^4$ and $X^5$ are as defined in formula (IV) above, with an amine of formula $HNY^4Y^5$ wherein $Y^4$ and $Y^5$ are as defined in formula (IV) above, with a peroxyacid, e.g. 3-chloroperbenzoic acid, preferably in an inert solvent, such as dichloromethane, at a temperature from about 0° C. to about room temperature.

Intermediates of formulae (II) are novel compounds and, as such, they and their processes described herein for their preparation constitute further features of the present invention.

The present invention is further Exemplified but not limited by the following illustrative Examples and Reference Examples.

Mass spectra (MS) were recorded on a Micromass Platform II mass spectrometer fitted with an Electrospray source and an HP1100 liquid chromatograph; using a mixture of acetonitrile and water (1:1, v/v) as the mobile phase, a flow rate of 0.3 ml/minute, an injection volume of 20 µl, a run time of 2.0 minutes, a scan range of 80-850 Daltons Positive/Negative, a scan time of 2.0 seconds, an ESI voltage of 3.5 Kv, an ESI pressure of 20 n/m2 Nitrogen. Abbreviations have the following significances: w=weak.

EXAMPLE 1

(a) 4-[5-(5,5-Dimethyl-[1,3]dioxan-2-yl)-2-(4-fluoro-phenyl)-2H-pyrazol-3-yl]-pyridine A solution of 4-[5-dimethoxymethyl-2-(4-fluoro-phenyl)-2H-pyrazol-3-yl]-pyridine (3 g, Reference Example 1), 2,2-dimethylpropane-1,3-diol (2.2 g) and p-toluene sulfonic acid (2 g) in dry toluene (50 ml) was refluxed for 1 hour with azeotropic removal of water. The reaction mixture was cooled to room temperature then evaporated. The residue was partitioned between ethyl acetate (50 ml) and saturated aqueous sodium carbonate solution (50 ml). The organic phase was washed three times with water (50 ml), then dried over magnesium sulphate and then evaporated. The residual oil was triturated twice with diethyl ether then recrystallised from diethyl ether to give the title compound as white needles (1 g), m.p. 150-151° C. [Elemental analysis: C,67.69; H,5.98; N,12.09%. Calculated for $C_{20}H_{20}FN_3O_2$: C,67.97; H,5.70; N,11.89%]. MS: 354 $[MH]^+$. $R_F$=0.42 (ethyl acetate, determined by thin layer chromatography on silica).

(b) by proceeding in a similar manner to Example 1(a) but using 4-[5-diethoxymethyl-2-(4-fluoro-phenyl)-2H-[1,2,4]triazol-3-yl]-pyridine (Reference Example 3) there was prepared 4-[5-(5,5-dimethyl-[1,3]dioxan-2-yl)-2-(4-fluoro-phenyl)-2H-[1,2,4]triazol-3-yl]-pyridine as a yellow solid, m.p. 125-127° C. [Elemental analysis: C, 64.38; H, 5.48; N, 16.11%. Calculated for $C_{19}H_{19}FN_4O_2$: C, 64.40; H, 5.40; N, 15.81%]. MS: 355 $[MH]^+$. $R_F$=0.42 (ethyl acetate, determined by thin layer chromatography on silica).

(c) by proceeding in a similar manner to Example 1(a) but using 4-[2-formyl-5-(4-fluoro-phenyl)-oxazol-4-yl]-pyridine [Reference Example 5(a)] there was prepared 4-[2-(5,5-dimethyl-[1,3]dioxan-2-yl)-5-(4-fluoro-phenyl)-oxazol-4-yl]-pyridine as a yellow solid, m.p. 141.2-142.5° C. [Elemental analysis: C, 67.44; H, 5.18; N, 7.87%. Calculated for $C_{20}H_{19}FN_2O_3$: C, 67.79; H, 5.40; N, 7.90%]. MS: 355 $[MH]^+$. $R_F$=0.28 (ethyl acetate, determined by thin layer chromatography on silica).

(d) by proceeding in a similar manner to Example 1(a) but using 4-[2-formyl-4-(4-fluoro-phenyl)-oxazol-5-yl]-pyridine [0.9 g, Reference Example 5(b)] and subjecting the crude reaction product to flash chromatography on silica eluting with ethylacetate followed by recrystallisataion from diethyl ether there was prepared 4-[2-(5,5-dimethyl-[1,3]dioxan-2-yl)-4-(4-fluoro-phenyl)-oxazol-5-yl]-pyridine as a white solid, m.p. 138-140° C. MS: 355 [MH]$^+$. R$_F$=0.42 (ethyl acetate, determined by thin layer chromatography on silica).

(e) by proceeding in a similar manner to Example 1(a) but reacting (i) 4-[5-dimethoxymethyl-2-(4-fluoro-phenyl)-2H-pyrazol-3-yl]-pyridine, (ii) 4-[5-diethoxymethyl-2-(4-fluoro-phenyl)-2H-[1,2,4]triazol-3-yl]-pyridine, (iii) 4-[2-formyl-5-(4-fluoro-phenyl)-oxazol-4-yl]-pyridine or (iv) 4-[2-formyl-4-(4-fluoro-phenyl)-oxazol-5-yl]-pyridine with 3-hydroxy-2-(hydroxymethyl)-2-methyl-1-morpholino-1-propanone (prepared according to the method described for Reference Example 6 in International Patent Application No. WO98/56788) instead of 2,2-dimethylpropane-1,3-diol there may be prepared {2-[1-(4-fluoro-phenyl)-5-pyridin-4-yl-4H-pyrazol-3-yl]-5-methyl-[1,3]dioxan-5-yl}-morpholin-4-yl-methanone, {2-1-(4-fluoro-phenyl)-5-pyridin-4-yl-1H-[1,2,4]triazol-3-yl]-5-methyl-[1,3]dioxan-5-yl}-morpholin-4-yl-methanone, {2-[5-(4-fluoro-phenyl)-4-pyridin-4-yl-oxazol-2-yl]-5-methyl-[1,3]dioxan-5-yl}-morpholin-4-yl-methanone and {2-[4-(4-fluoro-phenyl)-5-pyridin-4-yl-oxazol-2-yl]-5-methyl-[1,3]dioxan-5-yl}-morpholin-4-yl-methanone.

REFERENCE EXAMPLE 1

4-[5-Dimethoxymethyl-2-(4-fluoro-phenyl)-2H-pyrazol-3-yl]-pyridine

A stirred solution of 4,4-dimethoxy-1-pyridin-4-yl-butane-1,3-dione (20 g, Reference Example 2) in ethanol (500 ml) was treated with 4-fluorophenylhydrazine hydrochloride (29 g). The mixture was refluxed for 0.5 hour then evaporated. The residual yellow oil was subjected to flash chromatography on silica eluting with a mixture of methanol and dichloromethane (99:1, v/v) to give the title compound as a brown oil (2.7 g). MS: 314 [MH]$^+$. R$_F$=0.27 (ethyl acetate, determined by thin layer chromatography on silica).

REFERENCE EXAMPLE 2

4,4-Dimethoxy-1-pyridin-4-yl-butane-1,3-dione

A solution of 4-acetylpyridine (12 g) in dry tetrahydrofuran (500 ml), under nitrogen and at −60° C., was treated with a solution of lithium bis(trimethylsilyl)amide in hexane (200 ml, 1M). The mixture was allowed to warm to −40° C. then treated with methyl dimethoxyacetate (12 ml). After standing at room temperature for 16 hours the reaction mixture was evaporated and the residue was triturated with diethyl ether to give the title compound as a yellow solid (22 g).

REFERENCE EXAMPLE 3

4-[5-Diethoxymethyl-2-(4-fluoro-phenyl)-2H-[1,2,4]triazol-3-yl]-pyridine

A stirred solution of 4-fluorophenylhydrazino-diethoxyacetamidine (8 g, Reference Example 4) in dichloromethane (150 ml) was treated with isonicotinoyl chloride hydrochloride (5 g) then with triethylamine (8 ml). The mixture was stirred for 0.5 hour and then evaporated. The residual yellow oil was treated with toluene (200 ml) and the white solid filtered off. The filtrate was heated at reflux temperature for 1 hour in a Dean Stark apparatus and then evaporated. The residual oil was subjected to flash chromatography on silica eluting with ethyl acetate to give the title compound. MS: 343 [MH$^+$].

REFERENCE EXAMPLE 4

4-Fluorophenylhydrazino-diethoxyacetamidine

A solution of methyl diethoxyacetimidate (4.5 g, prepared according to the procedure described by Schaefer et al., J.Org.Chem., 1961, 26, pages 412-418) in methanol (150 ml) was treated with 4-fluorophenylhydrazine hydrochloride (4.53 g). After standing at room temperature for 16 hours the mixture was evaporated. The residue was treated with ethyl acetate and filtered. The filtrate was evaporated to give the title compound as a yellow oil. MS: 256 [MH$^+$].

REFERENCE EXAMPLE 5

(a) 4-[2-Formyl-5-(4-fluoro-phenyl)-oxazol-4-yl]-pyridine (compound H)

A stirred solution of 4-[5-(4-fluoro-phenyl)-oxazol-4-yl]-pyridine (1.5 g, Reference Example 6) in dry tetrahydrofuran (50 ml), under an inert atmosphere and at −10° C., was treated with a solution of lithium bis(trimethylsilyl)amide in tetrahydrofuran (12.5 ml, 1M). After 0.5 hour the mixture was treated with N-formylmorpholine (1.5 ml). This mixture was stirred at room temperature for 16 hours then treated with diethyl ether (50 ml) and then filtered. The solid was suspended in 10% aqueous ammonium chloride solution (50 ml) and the resulting yellow solid filtered to give the title compound. MS: 269 [MH$^+$].

(b) by proceeding in a similar manner to Reference Example 5(a) but using 4-[4-(4-fluoro-phenyl)-oxazol-5-yl]-pyridine (Reference Example 8) there was prepared 4-[2-formyl-4-(4-fluoro-phenyl)-oxazol-5-yl]-pyridine. MS: 269 [MH$^+$].

REFERENCE EXAMPLE 6

4-[5-(4-Fluoro-phenyl)-oxazol-4-yl]-pyridine

To a solution of 1-(4-fluoro-phenyl)-2-pyridin-4-yl-ethane-1,2-dione1-oxime (4.88 g, Reference Example 7) in formic acid (150 ml) was added zinc (3.9 g) and the resulting mixture was refluxed for 6 hours. The solvent was then evaporated, the residue taken up into ethyl acetate and the grey solid discarded. The solvent was evaporated and the oil was subjected to flash chromatography on silica eluting with ethyl acetate to give the title compound as a white solid. MS: 241 [MH]$^+$. R$_F$=0.28 (ethyl acetate, determined by thin layer chromatography on silica).

REFERENCE EXAMPLE 7

1-(4-Fluoro-phenyl)-2-pyridin-4-yl-ethane-1,2-dione1-oxime

A solution of 1-(4-fluoro-phenyl)-2-pyridin-4-yl-ethanone (6.45 g, prepared according to the method described for Reference Example 11 in the specification of International Patent Application No. WO98/56788) in acetic acid (50 ml) was treated with a solution of sodium nitrite (4.14 g) in water (30 ml) at 10° C. The reaction mixture was stirred at room temperature for 16 hours then treated with water (150 ml) and then filtered to give the title compound as a white solid.

REFERENCE EXAMPLE 8

4-[4-(4-Fluoro-phenyl)-oxazol-5-yl]-pyridine

A solution of 2-bromo-1-(4-fluoro-phenyl)-2-pyridin-4-yl-ethanone hydrobromide (10 g, Reference Example 9) in acetonitrile (100 ml) at 0° C. was treated with formic acid (10 ml) followed by triethylamine (35 ml). The solution was stirred at room temperature for 16 hours and urea (4 g) was added together with formic acid (100 ml). The resulting mixture was refluxed for 6 hours with concomitant removal of the acetonitrile [with a Mc Intire head]. The solvent was then evaporated, the residue taken up into ethyl acetate and the grey solid discarded. The solvent was evaporated and the resulting gum was dissolved in water (100 ml) and the solution basified to pH 11 by addition of sodium hydroxide pellets. The resulting solid was filtered and subjected to flash chromatography on silica eluting with ethyl acetate to give the title compound as a white solid. MS: 241 [MH$^+$]. R$_F$=0.34 (ethyl acetate, determined by thin layer chromatography on silica).

REFERENCE EXAMPLE 9

2-Bromo-1-(4-fluoro-phenyl)-2-pyridin-4-yl-ethanone

A solution of 1-(4-fluoro-phenyl)-2-pyridin-4-yl-ethanone (6.45 g) in dichloromethane (150 mL) was treated with bromine (1.5 ml). The reaction mixture was stirred at room temperature for 16 hours and the yellow solid formed filtered to give the title compound as the hydrobromide.

In Vitro and In Vivo Test Procedures

1. In Vitro Inhibitory Effects on TNF-Alpha Release by Human Monocytes

The effects of compounds on TNF-alpha production by human peripheral blood monocytes (PBMs) are examined as follows.

1.1. Preparation of Human Peripheral Blood Monocytes

Freshly drawn blood from normal healthy donors was mixed (4:1, v/v) with sodium citrate (3.8%, w/v). Mononuclear cells were prepared by centrifugation of the blood on Histopaque-1077 (Sigma Diagnostics) according to manufacturers instructions. The fraction enriched with mononuclear cells was washed and resuspended in Hank's balanced salts solution (HBSS) supplemented with deoxyribonuclease (37.5 U/ml) and human serum albumin (0.3%). Differential (cytospin) cell counts revealed that the mononuclear cell fraction routinely comprised 70-80% monocytes.

Cells from the mononuclear leukocyte fraction were centrifuged (200 g, 10 min, 20° C.), resuspended, at a density of 10$^6$ cells/ml, in RPMI 1640 containing foetal calf serum (FCS) (1%), penicillin (50 U/ml) and streptomycin (50 µg/ml) and allowed to adhere in 96 well plates. Following incubation (5% CO$_2$, 37° C.) for 90 minutes, medium containing non-adherent cells was removed, the cells were washed once with fresh medium and fresh medium was added.

1.2. Measurement of Monocyte TNF-Alpha Release

Adherent cells in culture medium were incubated for 1 hour (5% CO$_2$, 37° C.) with fresh medium containing compounds or vehicle (0.1% dimethylsulphoxide). Compounds were tested within the concentration range of 3×10$^{-9}$M to 3×10$^{-6}$M. LPS (10 ng/ml) was then added to the cells and the incubation continued for a further 18 hours. Cell supernatants were removed into 96 well, 0.22 µm filtration plates for storage at −20° C.

TNF-alpha concentrations in cell supernatants were quantified by sandwich ELISA. Briefly, ELISA plates were coated overnight with 2 µg/ml of mouse anti-human TNF-alpha antibody in bicarbonate buffer (pH 9.9). After washing the wells with wash buffer (0.05% (v/v) Tween in PBS), and blocking unoccupied sites (1% BSA in PBS), monocyte supernatant samples or human recombinant TNF-alpha standards were vacuum filtered into the corresponding wells of the ELISA plate. Biotinylated rabbit polyclonal anti-human TNF-alpha antibody (3 µg/ml) was used as the second antibody and streptavidin-horseradish peroxidase was used as the detection antibody. The peroxidase substrate was 3,3',5,5'-tetramethylbenzidine (TMB), in the presence of hydrogen peroxide.

TNFα concentrations in supernatants from control and LPS-stimulated monocyte incubations were calculated by interpolation from a standard (log/log) curve (0.125-16 ng/ml) fitted by linear regression using a Multicalc software program (Wallac U.K., Ltd).

1.3. Results

Compounds within the scope of the invention produce 50% inhibition of LPS induced TNF-alpha release from human monocytes at concentrations within the range of 10$^{-9}$ M to 10$^{-4}$ M, preferably within the range of 10$^{-9}$ M to 10$^{-7}$ M.

2. Inhibitory Effects of Compounds on Serum TNF-Alpha Levels in LPS-Challenged Mice 2.1. Treatment of Animals and Measurement of Murine TNF-Alpha.

Female Balb/c mice (age 6-8 weeks, weight 20-22 g from Charles River, U.K.) in groups of five or more animals were dosed p.o. with compounds (1 to 100 mg/kg) suspended in 1.5% (w/v) carboxymethyl cellulose then challenged after a minimum period of 30 minutes with 30 mg of LPS i.p. After 90 minutes, the animals were killed by carbon dioxide asphyxiation and bled by cardiac puncture. Blood was allowed to clot at 4° C., centrifuged (12,000 g for 5 minutes) and serum taken for TNF-alpha analysis. TNF-alpha levels are measured using a commercially available murine TNF-alpha ELISA kit, purchased from Genzyme (Cat. no. 1509.00), as recommended by the manufacturer. Values for TNF-alpha were calculated from a recombinant murine TNF-alpha standard curve as above.

Results

Compounds within the scope of the invention inhibit TNF-alpha release in LPS challenged mice up to 50% at doses of 0.1 mg/kg to 100 mg/kg.

The invention claimed is:

1. A compound of formula (I):

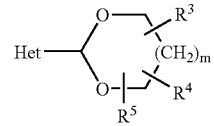

wherein:—
Het is a five heteroaromatic ring of the formula

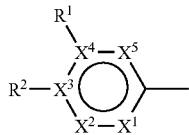

in which $R^1$ is optionally substituted aryl, and $R^2$ is 4-pyridyl; wherein aryl is selected from: phenyl and naphthyl; and aryl optional substitution is with one or more substituents selected from: acyl, acylamino, alkoxy, ailcoxycarbonyl, alkylenedioxy, alkylsulphinyl, alkylsulphonyl, allcylthio, aroyl, aroylamino, aryl, arylailcyloxy, arylailcyloxycarbonyl, arylallcyltbio, aryloxy, aryloxycarbonyl, arylsulphinyl, arylsulphonyl, arylthio, carboxy, cyano, halo, hydroxy, nitro, trifluoromethyl, $Y^3Y^4N$—, $Y^3Y^4NCO$—, $Y^3Y^4NSO_2$—, $Y^3Y^4N$—$C_{2-6}$ alkylene-$Z^1$- (where $Z^1$ is O, $NR^5$ or S(O)n), alkylC(=O)—$Y^3N$—, alkylSO$_2$—$Y^3N$—or alkyl optionally substituted with aryl hydroxy, or $Y^3Y^4N$—;

$X^2$ is CH, $X^3$ is C, $X^4$ is N and $X^5$ is N;

$R^3$ represents a group -$L^1$-$R^6$;

$R^4$ represents hydrogen, alkyl or hydroxyalkyl; or $R^3$ and $R^4$, when attached to the same carbon atom, may form with the said carbon atom a cycloalkyl, cycloalkenyl or heterocycloalkyl ring or a group C=CH$_2$;

$R^5$ represents hydrogen or alkyl;

$R^6$ is hydrogen, alkyl, azido, hydroxy, alkoxy, aryl, arylalkyloxy, aryloxy, carboxy an acid bioisostere selected from the group consisting of C(=O) NHOH, —C(=O)—CH$_2$OH, —C(=O)—CH$_2$SH, C(=O) NH—CN, sulpho, phosphono, alkylsuiphonylcarbamoyl, arylsulphonylcarbamoyl, N methoxycarbamoyl, or 3 hydroxy-3-cyclobutene-1,2-dione, cycloalkyl, cycloalicyloxy, nitro, —NY$^1$Y$^2$, —N(R$^7$)—C(=Z)—R$^8$, —N(R$^7$)—C(=Z)-L$^2$-R$^9$, —NH—C(=Z)—NH—R$^8$, —NH—C(=Z)—NH-L$^2$-R$^9$, —N(R$^7$)—SO$_2$-R$^8$, —N(R$^7$)—SO$_2$-L$^2$-R$^9$, —S(O)$_n$R$^{10}$, —C(=Z)—NY$^1$Y$^2$ or —C(=Z)—OR$^{10}$;

$R^7$ is hydrogen, alkyl, aryl, arylalkyl, or cycloalkyl;

$R^8$ is alkyl, alkoxy, aryl, arylalkyloxy, or cycloalkyl,;

$R^9$ is alkoxy, aryl, arylalkyloxy, arylalkyloxycarbonylamino, carboxy, an acid bioisostere selected from the group consisting of C(=O) NHOH, —C(=O)—CH$_2$OH, -C(=O)-CH2SH, C(=O) NH—CN, suipho, phosphono, alkylsuiphonylcarbamoyl, arylsulphonylcarbamoyl, N methoxycarbamoyl, 3 hydroxy-3-cyclobutene-1,2-dione, cycloalicyl, cyano, halo, hydroxy or —NY$^3$Y$^4$;

$R^{10}$ is alkyl, aryl, arylalkyl, or cycloalkyl;

$L^1$ represents a direct bond or a straight- or branched-chain alkylene linkage containing from 1 to 6 carbon atoms and optionally substituted by halogen, hydroxy, alkoxy or oxo;

$L^2$ is a straight- or branched-chain alkylene linkage containing from 1 to 6 carbon atoms;

$Y^1$ and $Y^2$ are independently hydrogen, alkenyl, alkynyl, aryl, cycloalkyl, or alkyl optionally substituted by alkoxy, aryl, cyano, cycloalkyl, hydroxy, oxo, —CO$_2$R$^7$, —CONY$^3$Y$^4$ or —NY$^3$Y$^4$;

$Y^3$ and $Y^4$ are independently hydrogen, alkenyl, alkyl, alkynyl, aryl, arylalkyl, or cycloalkyl;

$Y^5$ is hydrogen, alkyl, aryl, arylalkyl, —C(=Z)R$^{10}$, —C(=Z)OR$^{10}$ or —SO$_2$R$^{10}$;

Z is an oxygen or sulphur atom;

m is zero or an integer 1 or 2; and n is zero or an integer 1 or 2;

or an N-oxides thereof, or a pharmaceutically acceptable salt thereof.

2. A compound according to claim 1 in which $R^3$ and $R^4$ are both $C_{1-4}$ alkyl groups.

3. A compound according to claim 1 in which $R^3$ is —C(=O)—NY$^1$Y$^2$ (where Y$^1$ and Y$^2$ are as defined in claim 1) and $R^4$ is $C_{1-4}$alkyl.

4. A compound according to claim 3 in which Y$^1$ is hydrogen and Y$^2$ is alkyl or cycloalkyl.

5. A pharmaceutical composition comprising a compound according to claim 1 together with a pharmaceutically acceptable carrier or excipient.

* * * * *